(12) United States Patent
Stadtfeld et al.

(10) Patent No.: US 10,443,043 B2
(45) Date of Patent: Oct. 15, 2019

(54) METHODS FOR MAKING INDUCED PLURIPOTENT STEM CELLS

(71) Applicants: Matthias Stadtfeld, New York, NY (US); Simon E. Vidal, New York, NY (US); Bhishma Amlani, New York, NY (US)

(72) Inventors: Matthias Stadtfeld, New York, NY (US); Simon E. Vidal, New York, NY (US); Bhishma Amlani, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/148,230

(22) Filed: May 6, 2016

(65) Prior Publication Data
US 2016/0326497 A1    Nov. 10, 2016

Related U.S. Application Data
(60) Provisional application No. 62/158,089, filed on May 7, 2015.

(51) Int. Cl.
*C12N 15/00* (2006.01)
*C12N 5/00* (2006.01)
*C12N 5/02* (2006.01)
*C12N 5/074* (2010.01)

(52) U.S. Cl.
CPC ........ *C12N 5/0696* (2013.01); *C12N 2501/15* (2013.01); *C12N 2501/415* (2013.01); *C12N 2501/602* (2013.01); *C12N 2501/603* (2013.01); *C12N 2501/604* (2013.01); *C12N 2501/606* (2013.01); *C12N 2506/1307* (2013.01)

(58) Field of Classification Search
CPC .................................................. C12N 5/0696
See application file for complete search history.

(56) References Cited

PUBLICATIONS

Woltjebn and Stanford 2009, Cell Stem Cell, 5:457-458.*
Silva 2008, plosone, 6:e253, pp. 2237-2247.*
Maherali 2009, Curr Biol, 19:1718-1723, provided as pp. 1-10.*
Ichida 2009, Cell Stem Cell, 5:491-503.*
Shi 2010, Cell Stem Cell, 6: 1-2.*
Woltjebn and Stanford ( 009, Cell Stem Cell, 5:457-458.*
Tsuji Neurotherapeutics, 2011, 8:668-676.*
MacDonald (2009, Developmental Cell, 17:9-26).*
Katoh, Cancer Biology and Therapy, 2006, 5:1059-1064.*
Willed, CSH Perspectives in Biology, 2012, 4:1-13.*
Heldin (2016, CSH Perspectives in Biology, 8:1-34).*
Thomson et al. (PNAS, 92:7844-7848 (Aug. 1995)).*
Stem Cells: Scientific Progress and Future Research Directions, Department of Health and Human Services, Chapter 1, pp. 14, Jun. 2001.*
Djuric and Ellis, 202, Stem Cell Research and Therapy, 2010,1:3.*
Chen et al, "Chemically defined conditions for human iPS cell derivation and culture", Nat Methods, 2011, 8:424-429.
Chen et al, "Rational optimization of reprogramming culture conditions for the generation of induced pluripotent stem cells with ultra-high efficiency and fast kinetics", Cell Research, 2011, 21:884-894.
Esteban et al, "Vitamin C enhances the generation of mouse and human induced pluripotent stem cells", Cell Stem Cell, 2010, 6:71-79.
Esteban et al, "Vitamin C improves the quality of somatic cell reprogramming", Nature Genetics, 2012, 44:366-367.
Li et al, "Small molecules that modulate embryonic stem cell fate and somatic cell reprogramming", Cell, 2009, 31:36-45.
Li et al, "Chemical approaches to studying stem cell biology", Cell Research, 2013, 23:81-91.
Marson et al, "Wnt signaling promotes reprogramming of somatic cells to pluripotency", Cell Stem Cell, 2008, 3:132-135.
Monfort et al, "Breathing-in epigenetic change with vitamin C", EMBO reports, 2013,14:337-346.
Polo et al, "A molecular roadmap of reprogramming somatic cells into iPS cells", Cell, 2012,151:1617-1632.
Stadtfeld et al, "Defining molecular cornerstones during fibroblast to iPS cell reprogramming in mouse", Cell Stem Cell, 2008, 2:230-240.
Stadtfeld et al, "Induced pluripotency: history, mechanisms, and applications", Genes & Development, 2010, 24:2239-2263.
Stadtfeld et al, "Ascorbic acid prevents loss of Dlk1-Dio3 imprinting and facilitates generation of all-iPS cell mice from terminally differentiated B cells", Nat Genetics, 2012, 44:398-405.
Vidal et al, "Combinatorial Modulation of Signaling Pathways Reveals Cell-Type-Specific Requirements for Highly Efficient and Synchronous iPSC Reprogramming", Stem Cell Reports, 2014, 3:1-11.
Wu et al, "Clinical Grade iPS Cells: Need for Versatile Small Molecules and Optimal Cell Sources", Cell, 2013, 1311-1322.
Zhang et al, "Small molecules, big roles—the chemical manipulation of stem cell fate and somatic cell reprogramming", Journal of Cell Science, 2012,125:5609-5620.
Wang et al, "The Histone Demethylases Jhdm1a/1b Enhance Somatic Cell Reprogramming in a Vitamin-C-Dependent Manner", Cell Stem Cell, 2011, 9:575-587.
Theunissen et al., Systematic Identification of Culture Conditions for Induction and Maintenance of Naive Human Pluripotency, Cell Stem Cell, 2014, 15:471-487.

* cited by examiner

*Primary Examiner* — Valarie E Bertoglio
(74) *Attorney, Agent, or Firm* — Hoffman & Baron, LLP

(57) ABSTRACT

In vitro methods for generating induced pluripotent cells (iPSCs) are disclosed herein. Also encompassed are recombinant iPSCs generated using these methods and methods of use thereof.

16 Claims, 12 Drawing Sheets
Specification includes a Sequence Listing.

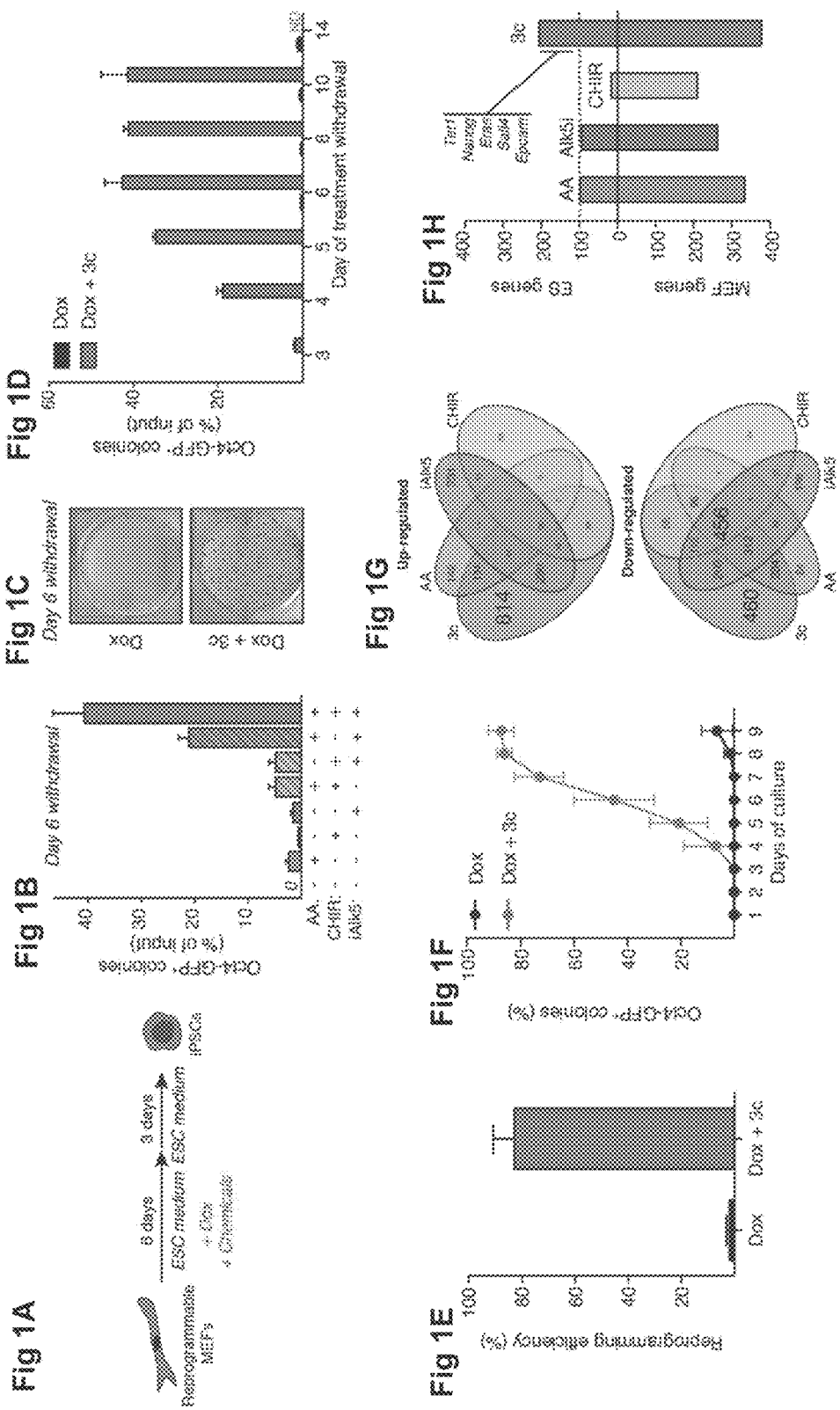

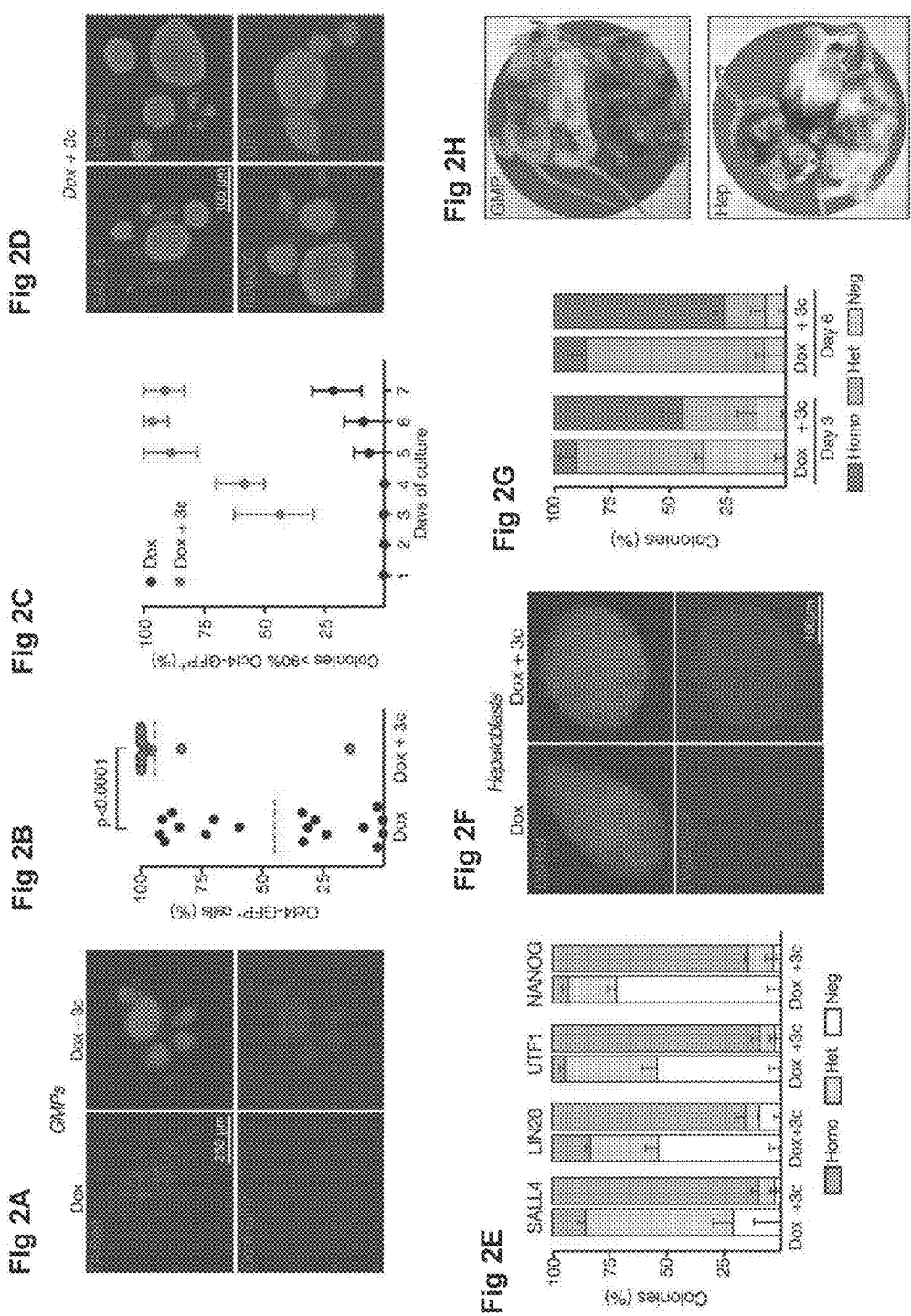

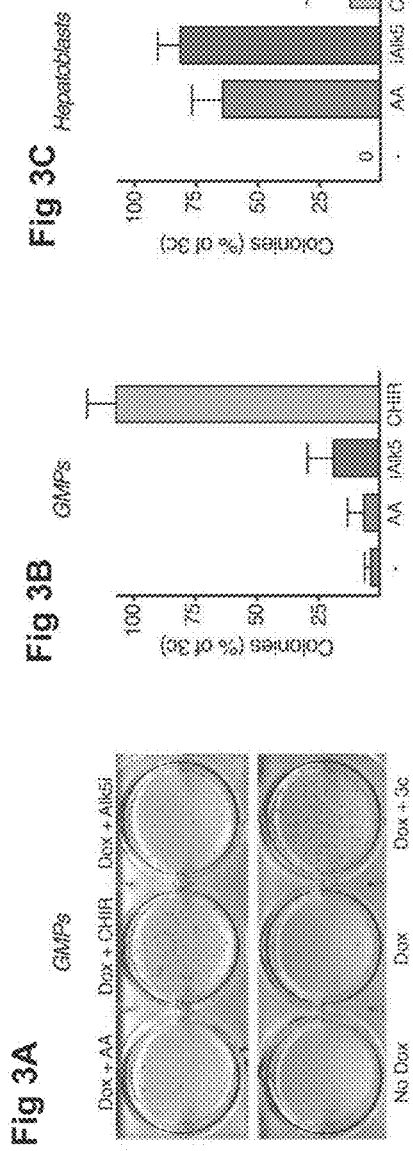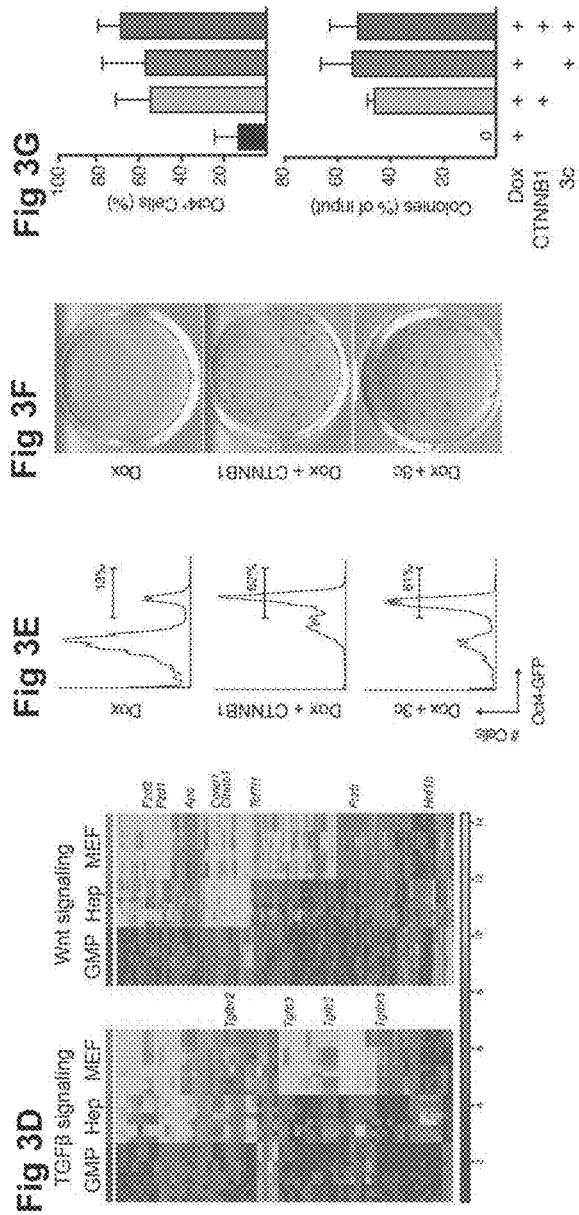

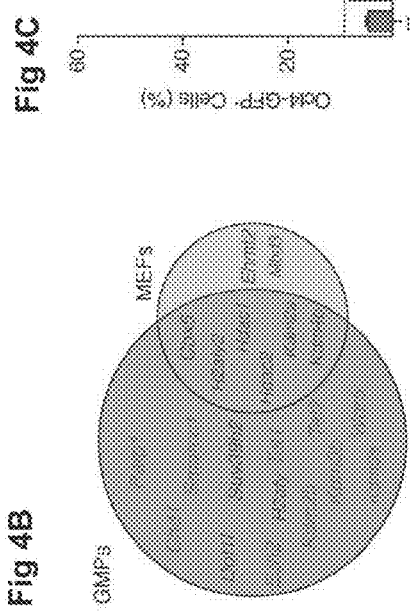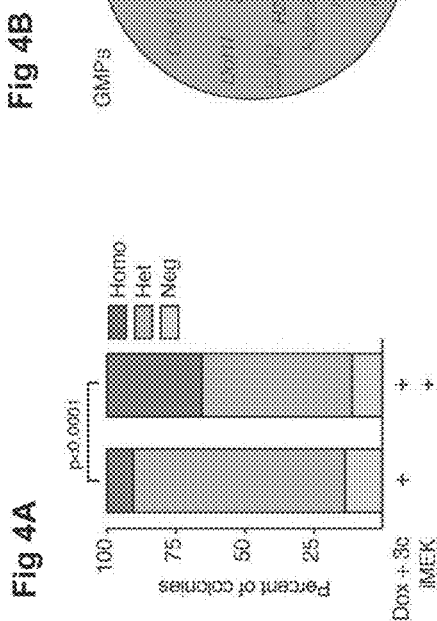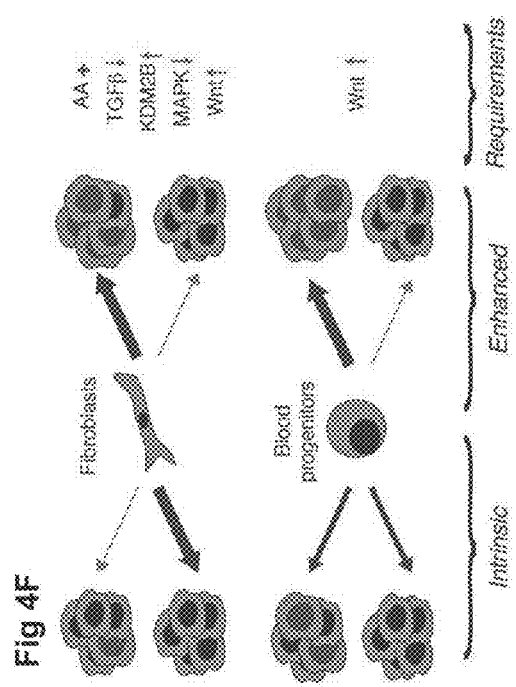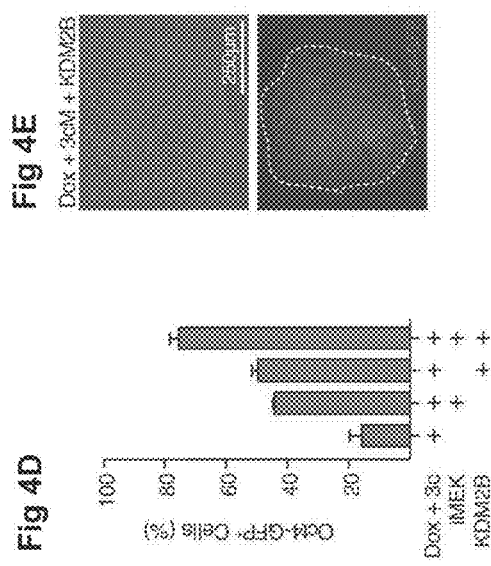

In both experiments reprogramming factors were expressed in somatic cells for 14 days.

*GMPs (Dox + CHIR)*

*GMPs*

*Hepatoblasts*

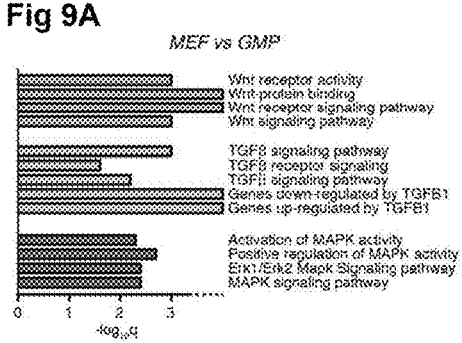
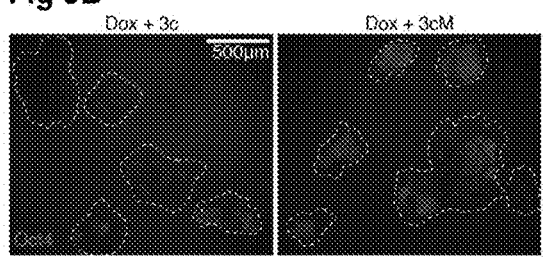
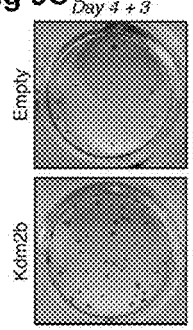
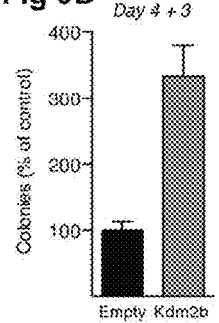
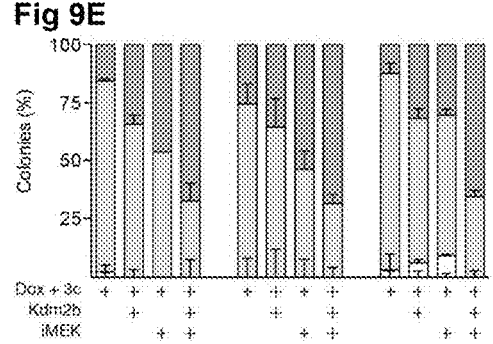

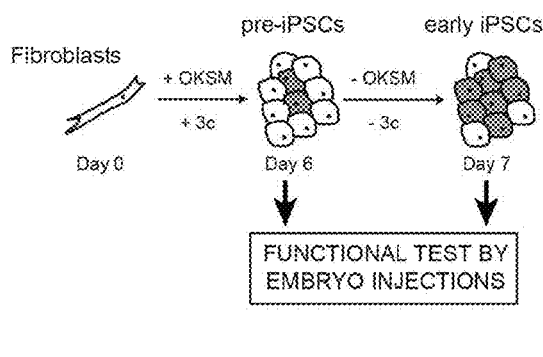 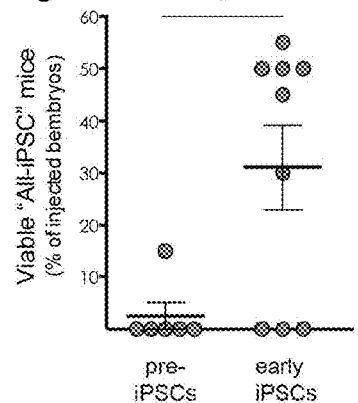
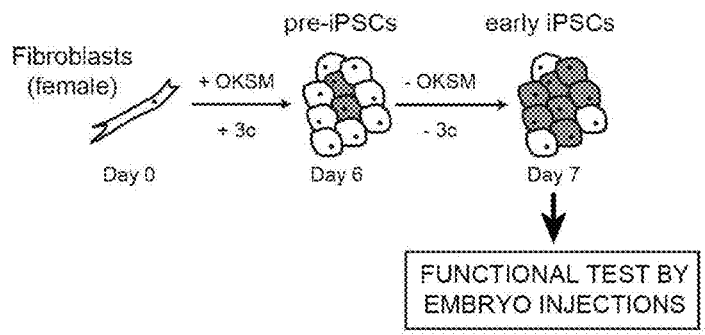 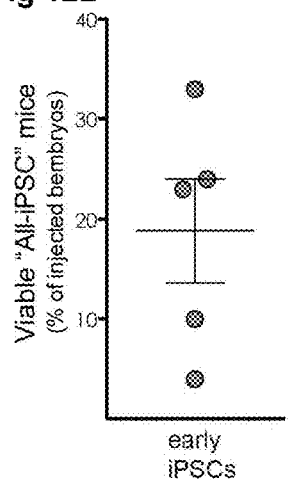

METHODS FOR MAKING INDUCED PLURIPOTENT STEM CELLS

CROSS REFERENCE TO RELATED APPLICATION

This application claims priority under 35 USC § 119(e) from U.S. Provisional Application Ser. No. 62/158,089, filed May 7, 2015, which application is herein specifically incorporated by reference in its entirety.

GOVERNMENT RIGHTS

The research leading to the present invention was funded in part by NIH/NICHD grant R21HD079883-01 and NIH/NIGMS grant 1R01GM111852-01. Accordingly, the United States government has certain rights in the invention.

FIELD OF THE INVENTION

The present invention pertains to the fields of cell culture and pluripotent stem cells (PSCs). More particularly, the invention relates to in vitro methods for making induced PSCs (iPSCs) from somatic cells. Populations of iPSCs generated using methods described herein are also encompassed, as are compositions comprising such iPSCs. Methods for using iPSCs and compositions thereof are also envisioned.

BACKGROUND OF THE INVENTION

Somatic cells can be reprogrammed into induced pluripotent stem cells (iPSCs) by the enforced expression of transcription factor combinations such as Oct4, Klf4, Sox2 and c-Myc (OKSM) (Takahashi and Yamanaka, 2006), generating a unique platform to study developmental processes and model disease in cell culture (Cherry and Daley, 2013). An intriguing hallmark of induced pluripotency is the comparatively low efficiency at which stable pluripotent cell lines are established, which ranges between 0.1 and 10% for most somatic cell types (Stadtfeld and Hochedlinger, 2010). This is associated with the asynchronous reactivation of endogenous pluripotency loci such as Oct4, Nanog and Utf1 and a lag phase of two or more weeks before a self-sufficient pluripotent state is established, which is only successful in a small subset of cells (Buganim et al., 2012; Polo et al., 2012). Studies in fibroblasts, the most commonly used cells for iPSC derivation, suggest that the gradual establishment of a chromatin environment permissive for OKSM activity may underlie these slow and stochastic reprogramming kinetics (Apostolou and Hochedlinger, 2013; Koche et al., 2011; Soufi et al., 2012). Intriguingly, some somatic cell types appear more amenable for the extensive epigenetic remodeling associated with acquisition of pluripotency. For example, within the hematopoietic system, immature progenitors form iPSCs more readily than differentiated cells (Eminli et al., 2009). The molecular reasons for this observation, however, remain unknown.

In agreement with the importance of chromatin remodeling for iPSC formation, small molecule compounds that alter the activity of chromatin-modifying enzymes can facilitate fibroblast reprogramming (Li et al., 2013). An example is the antioxidant ascorbic acid (AA), which serves as co-factor for α-ketoglutarate-dependent dioxygenases such as Tet proteins and Jmj C-domain-containing histone demethylases (Monfort and Wutz, 2013). Enhancement of iPSC formation has also been reported upon modulation of cellular signaling pathways. For example, activation of Wnt signaling by natural ligands (Marson et al., 2008) or chemical inhibition of GSK3 (Li and Ding, 2010), an antagonist of β-catenin, has been shown to promote iPSC formation. However, evidence for an inhibitory role of the Wnt pathway early in reprogramming has also been provided (Aulicino et al., 2014; Ho et al., 2013). Inhibition of TGFβ signaling supports both early (Li et al., 2010; Samavarchi-Tehrani et al., 2010) and late events (Ichida et al., 2009; Maherali and Hochedlinger, 2009) during the transition of fibroblasts to a pluripotent state.

Several publications and patent documents are referenced in this application in order to more fully describe the state of the art to which this invention pertains. The disclosure of each of these publications and documents is incorporated by reference herein.

SUMMARY OF INVENTION

The present inventors have investigated possible synergisms between compounds that affect chromatin modulators and cellular signaling pathways during iPSC reprogramming. In addition to fibroblasts, the present inventors focused on somatic progenitor cells with the goal to identify cell-intrinsic features that facilitate iPSC formation. Taking this approach, cell type specific requirements for the rapid and synchronous acquisition of pluripotency are described herein and provide molecular insight into why specific somatic cells are particularly amenable to reprogramming.

In one aspect, a method for generating induced pluripotent stem cells (iPSCs) is presented, the method comprising: providing at least one somatic cell exposed to exogenous reprogramming factors and culturing the at least one somatic cell in a first culture medium comprising a combination of agents comprising an activator of Wnt signaling, an inhibitor of transforming growth factor β(TGF-β), and ascorbic acid (AA), wherein the combination is in an amount effective to induce somatic cell reprogramming and the at least one somatic cell is cultured for an amount of time sufficient to induce reprogramming of the somatic cells, thereby generating induced pluripotent cells. An exemplary combination of an activator of Wnt signaling, an inhibitor of transforming growth factor β (TGF-β), and ascorbic acid comprises the GSK3b inhibitor CHIR99021 (CHIR), the TGFbeta antagonist ALK5 inhibitor II (iAlk5), and AA and is referred to as "3c" hereinafter.

In an embodiment thereof, the exposure to the exogenous reprogramming factors comprises introduction of exogenous nucleic acid sequences encoding the reprogramming factors into the at least one somatic cell. In a more particular embodiment, the exogenous nucleic acid sequences encoding the reprogramming factors are constitutively or inducibly expressed. Exogenous nucleic acid sequences may be introduced via viral transduction or transfection of mRNA or plasmid DNA.

In another embodiment, the at least one somatic cell is isolated from a transgenic mouse genetically engineered to express reprogramming factors in an inducible or constitutive fashion.

In one embodiment, the exogenous reprogramming factors comprise at least one of or all four of Oct4, Klf4, Sox2, and c-Myc. Exemplary nucleic acid sequences encoding reprogramming factors and proteins encoded thereby are designated and referred to herein as SEQ ID NOs: 1-16. More particularly, nucleic acid sequences encoding human Oct4, Klf4, Sox2, and Myc are referred to as SEQ ID NOs: 1, 3, 5, and 7, respectively; and corresponding human Oct4, Klf4, Sox2, and Myc proteins are referred to as SEQ ID NOs: 2, 4, 6, and 8, respectively. Nucleic acid sequences encoding mouse Oct4, Klf4, Sox2, and Myc are referred to as SEQ ID NOs: 9, 11, 13, and 15, respectively; and corresponding mouse Oct4, Klf4, Sox2, and Myc proteins are referred to as SEQ ID NOs: 10, 12, 14, and 16, respectively. In other embodiments, the exogenous reprogramming factors comprise at least one of Oct4, Sox2, and Esrrb; at least one of Nr5a1, Sox2, Klf4 and myc; at least one of Sall4, Nanog, Esrrb, Lin28; at least one of Oct4, Sox2 and myc; and at least one of Tet1, Sox2, Klf4 and myc. See, for example, Theunissen and Jaenisch, Cell Stem Cell 2014 Jun. 5; 14(6):720-34 doi: 10.1016/j.stem.2014.05.002, the entire content of which is incorporated herein by reference, for a review of suitable reprogramming factors.

In an embodiment, the amount of time sufficient to induce reprogramming of the somatic cells is 3-8 days, 2-5 days, or 5 days. In a more particular embodiment, the amount of time sufficient to induce reprogramming of the somatic cells is less than 7 days, is less than 6 days, is about 6 days, or is 6 days. In an even more particular embodiment, the amount of time sufficient to induce reprogramming of the somatic cells is one to four days, is one day, is about one day, is fours days, or is about four days. In another particular embodiment, the amount of time sufficient to induce reprogramming of the somatic cells is about one day, about two days, about three days, about four days, about five days, or about six days.

In a further particular embodiment, the at least one somatic cell is a fibroblast cell and the amount of time sufficient to induce reprogramming of the at least one somatic cell is about one day, about two days, about three days, about four days, about five days, about six days, about seven days, about eight days, or about nine days.

In yet another particular embodiment, the at least one somatic cell is a blood stem cell or blood progenitor cell and the amount of time sufficient to induce reprogramming of the at least one somatic cell is about one day, about two days, about three days, about four days, or about five days.

In a still further particular embodiment, the at least one somatic cell is a hepatoblast cell and the amount of time sufficient to induce reprogramming of the at least one somatic cell is about one day, about two days, about three days, about four days, or about five days.

In another embodiment, the method further comprises transferring the pluripotent cells from the first culture medium to a second culture medium that lacks the activator of Wnt signaling, the inhibitor of transforming growth factor β (TGF-β), and the ascorbic acid. In a still further embodiment, the method further comprises selecting the pluripotent cells based on maintenance of typical ESC-like morphology in the second culture medium that lacks the activator of Wnt signaling, the inhibitor of transforming growth factor β (TGF-β), and the ascorbic acid.

In yet another embodiment, the method further comprises selecting the pluripotent cells based on expression of at least one pluripotent marker. Exemplary pluripotent markers are known in the art and include ESSRB, NANOG, UTF1, endogenous SOX2, or endogenous Oct4 (also called Pou5f1).

In an embodiment of the method, the at least one somatic cell is a fibroblast, keratinocyte, immature or mature blood cell, or mature T or B cell. In a particular embodiment thereof, the at least one somatic cell is a mammalian somatic cell. Exemplary mammalian somatic cells comprise, without limitation: human, other primate, mouse, rat, pig, horse, dog, cat, sheep, goat, rabbit, camel, and cow somatic cells.

In a particular embodiment, the activator of Wnt signaling is an antagonist of GSK3. Exemplary activators of Wnt signaling include, without limitation, CHIR99021, recombinant Wnt3a, recombinant Norrin, recombinant R-spondin (Rspo), SB-216763, BIO (6-bromoindirubin-3'-oxime), or DCA.

In another particular embodiment, the inhibitor of TGF-β is ALK5 inhibitor II, A 83-01, GW 788388, LY 364947, RepSox, SB431542, SB505124, SB525334, D 4476, R 268712, SB 525334, or SD 208.

In a more particular embodiment, the combination of agents in an amount effective to induce somatic cell reprogramming is 0.1 microM to 30 microM of the activator of Wnt signaling, 25 nm to 2000 nm of the inhibitor of TGF-β, and 5 microgram/ml to 200 microgram/ml of ascorbic acid. In an even more particular embodiment, the combination of agents in an amount effective to induce somatic cell reprogramming is 0.5 microM to 10 microM of the activator of Wnt signaling, 100 nm to 1000 nm of the inhibitor of TGF-β, and 10 microgram/ml to 100 microgram/ml of ascorbic acid. In yet another particular embodiment, the combination of agents in an amount effective to induce somatic cell reprogramming is 2 microM to 4 microM of the activator of Wnt signaling, 200 nm to 500 nm of the inhibitor of TGF-β, and 25 microgram/ml to 75 microgram/ml of ascorbic acid.

In a still more particular embodiment, the combination of agents comprises CHIR99021, ALK5 inhibitor II, and ascorbic acid. In exemplary fashion, the combination of agents in an amount effective to induce somatic cell reprogramming is 3 µM CHIR99021, 250 nM TGF-β RI Kinase Inhibitor II, and 50 ng/µl L-ascorbic acid.

In an aspect, induced pluripotent stem cells (iPSCs) generated by methods described herein are envisioned, as are compositions comprising same. iPSCs so generated do not express genes characteristic of a differentiation state of the at least one somatic cell from which the iPSCs are induced and the iPSCs maintain correct imprinting at gene loci selected from the group consisting of Igf2-H19 and Dlk1-Dio3. See, for example, Ma et al. (2014, Nature 511:177-183); Plasschaert et al. (2014, Development 141: 1805-1813); Chang et al. (2014, Cell Res 24:293-306); and Stadtfeld et al. (2010, Nature 465:175-181); the entire content of each of which is incorporated herein by reference. Also envisioned herein are induced pluripotent stem cells (iPSCs) and compositions thereof, wherein the iPSCS are recombinant iPSCS that comprise exogenous nucleic acid sequences encoding reprogramming factors. Also envisioned are induced pluripotent stem cells (iPSCs) generated by methods described herein and compositions thereof.

Also envisioned herein are methods for using the induced pluripotent stem cells and compositions thereof. Such methods include drug testing of patient-specific iPSCs, tissue replacement using patient-specific iPSCs; in vitro modeling of degenerative diseases using patient-specific pluripotent cells; identification of genes, signaling pathways and environmental conditions influencing the derivation of pluripotent stem cell lines; and generation of model animals with a desired genetic background or specific T cell receptor or immunoglobulin rearrangements.

In a particular embodiment of a method for using iPSCs to generate an animal model with a desired genetic background, iPSCs generated using methods described herein can be used to generate entirely iPSC-derived mice by tetraploid embryo complementation. The utility of the present methods for the aforementioned purposes is underscored by the surprising rapidity with which the present methods generate iPSCs of high quality and in sufficient numbers to generate "all iPSC" animals. See, for example, FIGS. 10-12.

In accordance with the above, methods for making iPSCs, as described herein, further comprise injecting the iPSCs into a mammalian embryo to generate a mammal with a desired genetic background. In a particular embodiment thereof, the mammalian embryo is a blastocyst. In a further embodiment thereof, the mammalian embryo is a diploid blastocyst and the mammal with the desired genetic background is a chimeric animal comprising cells derived from the iPSCs. In yet another embodiment, the mammalian embryo is a tetraploid blastocyst and the mammal with the desired genetic background is entirely comprised of cells derived from the iPSCs.

In yet another particular embodiment, iPSCs generated using methods described herein or specific somatic cell types derived from these iPSCs can be administered to a subject in need thereof. A subject in need thereof may be, for example, a subject afflicted with a genetic condition or an injury that caused or led to tissue damage and administering the iPSCs or specific somatic cell types derived from such iPSCs to the subject promotes repair of the tissue damage. In a more particular embodiment thereof, the tissue may be absent from the subject or present in limited amounts that require supplementation for restoration of normal tissue function. In a more particular embodiment, the iPSCs or specific somatic cell types derived from such iPSCs are administered to the subject in a localized fashion to the specific site or sites of the injury or missing tissue so as to promote repair of the tissue damage or restoration of normal tissue function at the specific site or sites.

Other features and advantages of the invention will be apparent from the following description of the particular embodiments thereof, and from the claims.

BRIEF DESCRIPTION OF THE DRAWINGS

FIG. 1A-1H. Effect of combined TGFβ inhibition, Wnt activation and ascorbic acid on fibroblast reprogramming. (1A) Approach to identify chemicals that allow MEF reprogramming in six days or less. (1B) Percentage of dox-independent colonies that formed in presence of indicated compounds after six days of exogenous OKSM expression. Shown is mean and range of two independent experiments. (1C) Representative alkaline phosphatase (AP) staining of dox-independent colonies that formed after six days from 500 input MEFs. (1D) Percentage of dox-independent colonies derived after withdrawal of compound on the indicated day (mean and range of two independent experiments). ND=determined. (1E) Percentage of 96-well plate wells seeded with individual DsRed$^+$ reprogrammable MEFs that gave rise to dox-independent Oct4-GFP$^+$ colonies after twelve days in dox (n=3 experiments) or seven days in dox+3c (n=5 experiments). Error bars show standard deviations. (1F) Percentage of nascent colonies that contained Oct4-GFP$^+$ cells at the indicated day of reprogramming. Error bars indicate standard deviations of three independent experiments with at least 20 colonies analyzed. (1G) Venn diagrams of genes at least 1.5 fold up- or down-regulated in reprogramming intermediates derived in presence of indicated compounds compared to dox alone. (1H) Quantification of the top ESC-specific and MEF-specific genes that showed significant gene expression changes in intermediates derived in presence of indicated compounds compared to dox alone. Select ESC-associated genes exclusively upregulated in dox+3c are indicated. See also FIG. 6.

FIG. 2A-2H. Reprogramming of blood progenitors and hepatoblasts in 3c conditions. (2A) Representative images of Oct4-GFP and DsRed expression in colonies formed from individual GMPs after six days of culture. Note that most DsRed$^+$ cells are Oct4-GFP$^+$ in dox+3c but not in dox alone. (2B) Percentage of Oct4-GFP$^+$ cells in wells undergoing reprogramming after single cell seeding of GMPs and culture for six days in dox only (n=18 clonal colonies) or dox+3c (n=20 clonal colonies). (2C) Percentage of clonal GMP-derived colonies in which at least 90% of cells were Oct4-GFP$^+$ at the indicated time points. Shown is mean and range of two or three independent experiments, with at least 30 colonies analyzed. (2D) Representative superimposed images of GMP-derived colonies on day 4 of reprogramming in dox+3c after immunostaining against indicated pluripotency markers and counterstaining with DAPI. (2E) Quantification of GMP-derived colonies that express indicated pluripotency markers on day 4 of reprogramming in homogenous (>90% of positive cells), heterogeneous (1-90% of positive cells) fashion or are marker negative (<1% of positive cells). Shown are means and range of two independent experiments with 14 or more colonies scored each. (2F) Representative fluorescence microscopy images of hepatoblast-derived colonies after culture for six days. (2G) Quantification of Oct4 expression in hepatoblast-derived colonies on days 3 and 6 of reprogramming as defined for panel E. Shown are means and range of two independent experiments with 15 or more colonies scored each. (2H) Images of chimeric mice obtained after blastocyst injection of hepatoblast-iPSCs and GMP-iPSCs derived in dox+3c. See also FIG. 7.

FIG. 3A-3G. Modulation of specific signaling pathways during progenitor cell reprogramming. (3A) AP staining of dox-independent colonies after six days of culture of 100 reprogrammable GMPs in the presence of the indicated compounds. (3B) Quantification of dox-independent colonies derived from GMPs and (3C) hepatoblasts after six days of reprogramming in the presence of dox and indicated compounds. Colony numbers were normalized to values obtained in dox+3c. Error bars represent the range of two independent experiments with at least 50 colonies for GMPs and 14 for hepatoblasts scored in each experiment and condition. (3D) Heatmap showing TGFβ and Wnt associated genes differentially expressed (fold-change>3; q<0.05) in GMPs, hepatoblasts and MEFs. Select genes are highlighted. (3E) Representative flow cytometry plots showing Oct4-GFP expression after culture of 100 blood progenitor cells transduced with either empty or β-catenin virus. (3F) AP staining of dox-independent colonies formed after six days from blood progenitor cells transduced with empty or β-catenin virus. (3G) Quantification of Oct4 expression and colony formation formed after transducing blood progenitor cells with empty or β-catenin virus (n=3 wells seeded with transduced cells for each condition). See also FIG. 8.

FIG. 4A-4F. Factors facilitating synchronous MEF reprogramming. (4A) Quantification of MEF-derived colonies that express Oct4 in a homogenous or heterogeneous manner or that are negative after seven days of culture in dox+3c or dox+3 cM. The results are representative of three independent experiments with at least 80 colonies scored. P values for homogenous colonies were determined with Fisher's exact test. (4B) Venn diagram showing whether chromatin regulators implicated in enhancing (green) or repressing (red) reprogramming are higher expressed in GMPs (blue circle) or MEFs (brown circle). Gene names in bold indicate higher expression in pluripotent cells than in MEFs. (4C) Quantification of Oct4-GFP expression upon ectopic expression of indicated chromatin regulators in reprogrammable MEFs cultured in dox+3c for eight days. P values were calculated with one-way ANOVA (n=3 or more independent transduction experiments). (4D) Quantification of Oct4-GFP expression in colonies derived upon transduction with empty or Kdm2b virus and culture for eight days in dox+3c or +3 cM (n=3). (4E) Representative phase contrast and fluorescence images showing Oct4 expression in a colony obtained after Kdm2b expression in dox+3 cM. (4F) Model depicting characteristic features of the intrinsic and enhanced reprogramming response of fibroblasts and blood progenitor cells upon OKSM expression. Cell type-specific requirements for achieving enhanced reprogramming—such as repression of TGFβ signaling and increased activity of Kdm2b in fibroblasts—are shown. Accumulations of cells represent clonal colonies, with green cells successfully reprogramming and grey cells failing to reprogram. Thickness of arrows indicates the proportion of particular types of colonies that are observed under given conditions. See also FIG. 9.

FIG. 9A-9E. Related to FIG. 4. (9A) Gene ontology terms related to cell signaling that were significantly enriched in public microarray datasets for MEFs over GMPs. (9B) Representative fluorescence microscopy images of Oct4-GFP expression of MEF-derived colonies reprogrammed under dox+3c or dox+3 cM for six days. Colony borders are highlighted by dotted lines. (9C) Representative AP staining of dox-independent colonies after equal amounts of reprogrammable MEFs transduced with empty or Kdm2b virus were cultured for four days in dox+3c followed by three days in-basal ESC medium. (9D) Quantification of the number of the colonies obtained as described in panel 9C (n=3 wells seeded with transduced cells). (9E) Percentage of MEF-derived colonies that express the indicated pluripotency markers upon transduction with empty or Kdm2b virus and after 8 days of culture in the indicated conditions. Shown are mean and range of two independent experiments with at least 30 colonies scored. Het=1-90% cells marker positive; Homo=>90% cells marker positive; Neg=<1% cells marker positive.

FIG. 11A-11B. Rapid establishment of developmental potency. (11A) Scheme illustrating the reprogramming approach and showing at what stage cells were used for embryo injection (11B) Frequency of successful "All-iPSC" mice derivation from pre-iPSCs (not pluripotent) and early iPSCs (pluripotent), indicating that developmental potency in this system is immediately acquired after reprogramming is completed (=upon cessation of exogenous OKSM expression and chemical withdrawal).

FIG. 12A-12B. Developmental potency of female iPSCs. (12A) Scheme illustrating the reprogramming of female fibroblasts and showing at what stage these cells were used for embryo injection. (12B) Frequency of successful "All-iPSC" mice derivation from female iPSCs, showing that 3c allows robust induction of full developmental potency in female cells.

DETAILED DESCRIPTION OF THE INVENTION

The differentiated state of somatic cells provides barriers for the efficient derivation of induced pluripotent stem cells (iPSCs). To address why some cell types reprogram more readily than others, the present inventors studied the effect of combined modulation of cellular signaling pathways. This revealed that inhibition of TGFβ together with activation of Wnt signaling in the presence of ascorbic acid surprisingly allows >80% of murine fibroblasts to acquire pluripotency after one week of reprogramming factor expression. In contrast, hepatic progenitors and blood progenitors predominantly required only TGFβ inhibition or canonical Wnt activation, respectively, to reprogram at efficiencies approaching 100%. Strikingly, blood progenitors reactivated endogenous pluripotency loci in a highly synchronous manner. The present inventors further demonstrate that expression of specific chromatin-modifying enzymes and reduced TGFβ/MAP kinase activity are intrinsic properties associated with the unique reprogramming response of these cells. Inhibition of TGFβ together with activation of Wnt signaling in the presence of ascorbic acid also surprisingly accelerated the acquisition of pluripotency in iPSCs derived from murine keratinocytes and B lymphocytes. Together, observations presented herein define cell type-specific requirements for the rapid and synchronous reprogramming of somatic cells. See also Vidal et al. (2014, Stem Cell Reports 3:574-584), the entire content of which is incorporated herein by reference.

Generally speaking, the present inventors have determined that the amount of time sufficient to induce reprogramming (acquisition of pluripotency) of various somatic cells is approximately 2-3 days incubation time in culture medium comprising the 3c combination and the maximum number of iPSC colonies are observed by 6-8 days incubation time in culture medium comprising the 3c combination. These results are dramatically accelerated relative to previous described methods wherein the minimum time required to induce iPSCs is 10-12 days and maximum numbers of iPSCs are detected only after 2-3 weeks incubation time in inducing conditions.

The surprising nature of the present inventors' findings is underscored by the fact that initial reports demonstrated that the reprogramming-enhancing effects of the individual chemicals were rather modest and no dramatic decrease in the time needed for reprogramming was reported. In light of these initial reports, therefore, a modest additive effect was the most reasonable expectation for combinations of these chemicals. See, for example, Marson et al. (2008, Cell Stem Cell. 3:132-135), Maherali et al. (2009, Curr Biol 19:1718-1723), and Esteban et al. (2010, Cell Stem Cell. 6:71-79); the entire content of each of which is incorporated herein by reference.

Figure 13:
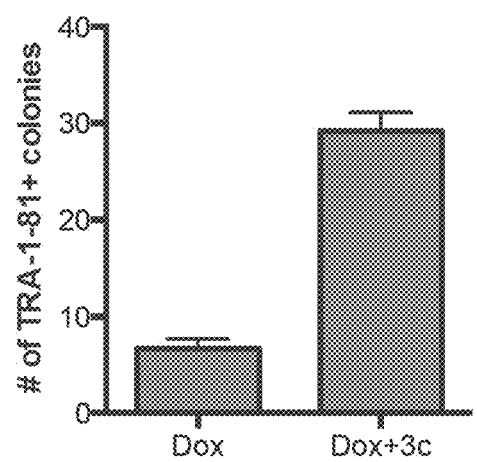
FIG. 13. Human blood progenitor cells were transduced with viruses encoding rtTA and doxycycline inducible OKSM and cultured in the presence of Dox or Dox+3c for two weeks. Shown are mean±standard error of number colonies which stained positive for TRA-1-81 (n=4 per treatment).

Also presented herein are results demonstrating that the addition of the 3c compounds to reprogramming media significantly increases the number of iPSC colonies derived from human blood progenitors transduced with viruses expressing the OKSM reprogramming factors. This is evidenced by assessing the expression of the stringent marker Tra-1-81 to identify colonies, the number of which was increased by about six-fold relative to Dox alone. See, for example, FIG. 13. These findings provide proof of concept that the enhancing effect of the 3c conditions is conserved among different mammals. The results presented herein are corroborated by the scientific literature, which supports the position that signaling pathways that contribute to iPSC generation are conserved among mammalian species. Further to this point, the literature reports, for example, that the same reprogramming factors—OKSM—have been shown to reprogram both mouse and human cells [Takahashi et al. (2006, Cell 126:663-676); Takahashi et al. (2007, Cell 131:861-872); the entire content of each of which is incorporated herein by reference]; that the enzymes targeted by the 3c compounds are highly conserved among mammals [Nordhoff et al. (2001, Mamm Genome 12:309-317); Goke et al. (2011, PLoS Comput Biol 7(12) e1002304); Liu et al. (2014, Nucleic Acids Res 42:4859-4867); Logan et al. (2004, Annu Rev Cell Dev Biol 20:781-810); the entire content of each of which is incorporated herein by reference]; and that at least two of the 3c compounds facilitate the induction of so-called naive pluripotency [Theunissen et al. (2014, Cell Stem Cell 15:471-487); the entire content of which is incorporated herein by reference].

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represents an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to provide a template-primer complex for the synthesis of the extension product.

Primers may be labeled fluorescently with 6-carboxyfluorescein (6-FAM). Alternatively primers may be labeled with 4, 7, 2', 7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More particularly, the preparation comprises at least 75% by weight, and most particularly 90-95% by weight of the given compound. Purity is measured by methods appropriate for the given compound (e.g. chromatographic methods, agarose or polyacrylamide gel electrophoresis, HPLC analysis, and the like).

"Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitate isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, viral transduction, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or combinations thereof. Immune responses may also involve the production or elaboration of various effector molecules such as cytokines, lymphokines and the like. Immune responses may be measured both in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

The term "about" as used herein refers to a variation in a stated value or indicated amount of up to 10%, 9%, 8%, 7%, 6%, 5%, 4%, 3%, 2%, 1%, 0.75%, 0.5%, 0.25% or 0.1%, wherein the variation can be either an increase or a decrease in the stated value or indicated amount. Use of the term may, therefore, be used to establish a range of values or amounts.

The term "pluripotent" as used herein refers to a cell that is capable of differentiating into more than one cell type (e.g., a differentiated cell type). In a particular embodiment, a pluripotent cell can differentiate into cell types characteristic of all three germ cell layers. The nude mouse teratoma formation assay is an exemplary assay used to determine if a cell is capable of differentiating into all three germ layers. The expression of embryonic stem (ES) cell markers may also be used to identify a pluripotent cell.

The term "reprogramming" as used herein refers to the process of altering the differentiated state of a somatic cell (e.g., a terminally-differentiated somatic cell) to a pluripotent phenotype.

The term "somatic cell" as used herein refers to a cell isolated from a subject (a primary cell) that is not, in its native form, pluripotent as defined herein above. Although many primary cells exhibit some loss of fully differentiated characteristics when cultured, simply culturing such cells does not render them pluripotent. The transition to pluripotency requires reprogramming stimuli that results in at least partial loss of differentiated character in culture. Reprogrammed pluripotent cells can also be passaged for extended periods of time without loss of growth potential. This is in marked contrast to primary cell progenitors from which they are derived, which generally have limited capacity for proliferative cycles in culture.

The term "activator of Wnt signaling" as used herein refers to a compound or factor that increases the expression of Wnt target genes, in most cases by activating the key Wnt transcription factor beta-catenin (also known as Ctnnb1). A compound or factor can do so by, for example, inhibiting degradation of beta-catenin, increasing expression of beta-catenin, or activating a co-factor of beta-catenin. Exemplary activators of Wnt signaling include, without limitation, CHIR99021, recombinant Wnt3a, recombinant Norrin, recombinant R-spondin (Rspo), SB-216763, BIO (6-bromoindirubin-3'-oxime), or DCA. Such agents are commercially available and can, for example, be purchased from Sigma, Tocris, Fisher, and Biovision.

The term "TGF-β signaling pathway" as used herein refers to downstream signaling events attributed to TGF-β and TGF-β like ligands. Engagement of Type II TGF-β receptors, for example, by a TGF-β ligand leads to the recruitment of Type I TGF-β receptors, which form heterodimers with Type II TGF-β receptors. Upon heterodimer formation, the Type I receptor is phosphorylated, which in turn phosphorylates and activates the SMAD family of proteins, thereby triggering a TGF-β signaling cascade. The signaling cascade ultimately leads to altered regulation of the expression of mediators involved in a variety of cellular processes, including, without limitation, cell growth, cell differentiation, tumorigenesis, apoptosis, and cellular homeostasis.

The term "inhibitor of the TGF-β signaling pathway" as used herein refers to inhibition of at least one of the proteins involved in the signal transduction pathway of TGF-β. Such inhibitors of the TGF-β signaling pathway encompass, for example, a TGF-β receptor inhibitor (e.g., a small molecule, an antibody, an siRNA), a TGF-β sequestrant (e.g., an antibody, a binding protein), an inhibitor of receptor phosphorylation, an inhibitor of a SMAD protein, or a combination of such agents.

In one embodiment, the TGF-β signaling pathway inhibitor comprises or consists essentially of a TGF-β receptor inhibitor. Assays for testing a compound to determine if it inhibits TGF-β receptor signaling are known in the art and are a matter of routine practice. Such assays may, for example, include determinations of phosphorylation status of the receptor or expression of downstream proteins controlled by TGF-β in cells cultured in the presence of the compound and comparing these determinations to those made for cells not treated with a TGF-β receptor inhibitor. An agent is identifed as a TGF-β signaling pathway inhibitor if the level of phosphorylation of the Type I TGF-β receptor in cells cultured in the presence of the agent is reduced by at least 20%, at least 30%, at least 40%, at least 50%, at least 60%, at least 70%, at least 80%, at least 90%, at least 95%, at least 99%, or even 100% (no phosphorylation) relative to the level of phosphorylation of the Type I TGF-β receptor in cells that are cultured in the absence of a TGF-β signaling pathway inhibitor.

Inhibitors of TGF-β receptor activity encompassed herein include, without limitation, an antibody, a small molecule, or an RNA interference molecule capable of inhibiting a TGF-β signaling pathway or combinations thereof. Exemplary inhibitors of TGF-β receptor activity also include the following compounds: A 83-01, D 4476, GW 788388, LY 364947, R 268712, RepSox, SB 431542, SB 505124, SB 525334, and SD 208. Such agents are commercially available and can, for example, be purchased from Sigma, Tocris, Fisher, and Biovision.

Small molecule inhibitors include, without limitation, 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole-.

The term "Alk5" as used herein refers to a TGF-β receptor type I having serine/threonine protein kinase activity (also referred to herein as TGFβR-1). The term "TGF-β receptor" or "TGFβR" as used herein encompasses all three sub-types of the TGFβR family (i.e., TGFβR-1, TGFβR-2, TGFβR-3). The TGFβ receptors all exhibit serine/threonine kinase activity and exist in several different isoforms that can be homo- or heterodimeric.

An "RNA interference molecule" as used herein refers to any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA), and small molecules which interfere with or inhibit expression of a target gene by RNA interference (RNAi).

In Vitro Methods

The in vitro methods described herein are based on the novel and surprising discoveries of the present inventors. By way of background, iPSCs can be derived from adult somatic cells by expression of specific transcriptional regulators such as, for example, the combination of Oct4, KIf4, Sox2 and myc (OKSM). This technology offers a unique avenue for the generation of patient-specific stem cell lines for basic and biomedical research as well as for drug screening and cell replacement therapy. Such applications are currently hampered by two major challenges. 1) iPSC derivation is a slow and inefficient process leading to high demands in terms of work load, costs and time to generate these cells; and 2) most iPSCs are of limited developmental potential, i.e., due to intrinsic errors they cannot generate all adult cell types. This deficiency limits their use for biomedical applications that require the ability to derive all adult cell types.

Figure 10A:
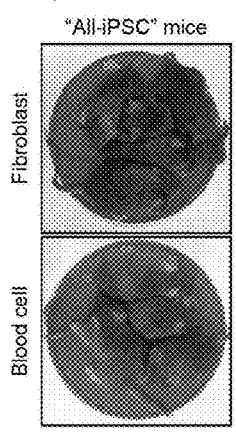
FIG. 10A-10C. Entire animals derived from 3c-iPSCs. (10A) Adult animals derived after tetraploid complementation conducted with iPSCs derived from either fibroblasts or blood cells treated in 3c conditions. (10B) Frequency of "All-iPSC" mice derivation from pluripotent cell lines established from fibroblasts (MEF) or blood cells (GMP) in 3c conditions. (10C) Example of animals derived from breeding "All-iPSC" mice with wildtype animals. Agouti coat color documents iPSC origin.
Figure 10B:
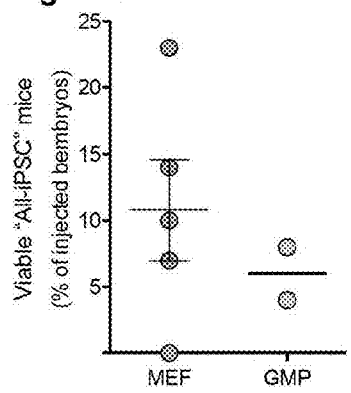
Figure 10C:
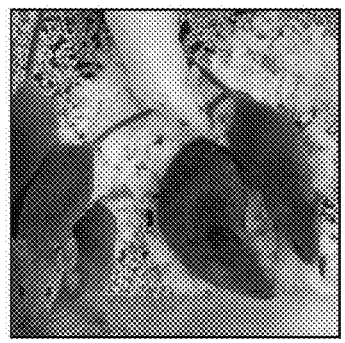

To address the deficiencies of prior art methods, the present inventors conducted a candidate screen of small molecular compounds to identify combinations that exert a strong synergistic effect on the formation of mouse iPSCs. This led to the identification of a three compound mix ("3c") consisting of ascorbic acid ("vitamin c"), the GSK3b inhibitor CHIR99021, and the TGFbeta antagonist ALK5 inhibitor II that increased the efficiency of iPSC formation upon OKSM expression from about 1% to about 80% of starting fibroblasts, the most commonly used cell type for iPSC derivation, and to >90% for blood progenitors cells, which for practical purposes are especially interesting sources for iPSC derivation in light of the minimally invasive procedures required to acquire such cells. In addition, the 3c compound mix facilitates rapid iPSC formation with reprogramming complete after only 4-6 days, which stands in contrast to the 2-3 weeks required under basal reprogramming conditions (consisting of mouse ESC media containing 15% fetal bovine serum (FBS) and leukemia inhibitory factor (LIF) but no chemical compounds). Further to this point, zero iPSCs are observed under standard reprogramming conditions in 4-6 days. It is also noteworthy that iPSCs derived under 3c conditions are able to differentiate in vivo into all adult cell types, as demonstrated by their ability to generate "All-iPSC" mice upon injection into tetraploid (i.e., developmentally impaired) blastocysts. See, for example, FIGS. 10 and 12.

In accordance with the discoveries of the present inventors, methods for generating induced pluripotent stem cells in vitro are presented herein. In one embodiment, the method comprises the steps of: providing at least one somatic cell comprising exogenous nucleic acid sequences encoding Oct4, Klf4, Sox2, and c-Myc and culturing the at least one somatic cell in a first culture medium comprising a combination of agents comprising an activator of Wnt signaling, an inhibitor of transforming growth factor β (TGF-β), and ascorbic acid, wherein the combination is in an amount effective to induce somatic cell reprogramming and the at least one somatic cell is cultured for an amount of time sufficient to induce reprogramming of the somatic cells, thereby generating induced pluripotent cells.

As taught herein, in vitro induction of PSCs from somatic cells may be evaluated or measured by detecting the expression of a PSC marker either at the RNA or the protein level. Such markers include ESSRB, NANOG, UTF1, endogenous Pou5f1 (also known as Oct4), and endogenous SOX2, expression of at least one of which is induced in a population of somatic cells incubated in accordance with the present method. Each of these cellular molecules (ESSRB, NANOG, UTF1, endogenous Pou5f1 (also known as Oct4) or endogenous SOX2 serves as a positive marker indicative of the generation of iPSCs. A change in expression of any of these markers may be determined using a variety of experimental protocols, including, but not limited to, immunohistochemistry, fluorescence activated cell sorting (FACS), and real-time PCR using appropriate primers. Experimental protocols that can be used to determine expression of such markers and relative expression levels are described in detail herein and are understood in the art.

Exemplary PSC markers include, without limitation, SSEA1, CD9, Lin28, Sall4, Nanog, Fbx15, Ecat1, EpCAM, Esg1, Eras, Gdf3, Fgf4, Cripto, Dax1, Zpf296, Slc2a3, Rex1, Utf1, and Nat1. See, for example, U.S. Pat. No. 8,603,818, the entire content of which is incorporated herein by reference.

The term "control substance", "control agent", or "control compound" as used herein refers a molecule that is inert or has no activity relating to an ability to modulate a biological activity. With respect to the present invention, such control substances are inert with respect to an ability to generate pluripotent cells from somatic cells in vitro. Exemplary controls include, but are not limited to, solutions comprising physiological salt concentrations.

Methods for Determining Expression Levels of Mammalian iPSC Markers

Based on the guidance presented herein and knowledge in the relevant scientific fields, the expression level of a cellular marker of mammalian iPSC can be determined using a variety of techniques. Exemplary markers of iPSCs include, but are not limited to, ESSRB, NANOG, UTF1, endogenous Pou5f1 (also known as Oct4) or endogenous SOX2. Expression levels of such markers may be assessed with respect to expressed nucleic acid corresponding to a cell marker (e.g., mRNA, total RNA) or with respect to polypeptides encoded by same. A variety of standard protocols may be used to determine, for example, RNA level, including, but not limited to: polymerase chain amplification and detection of amplified products therefrom, ribonuclease protection (RNase protection) assay, and Northern blot analysis. The principles and general procedures of each of these methods are described in, for example, Dvorak et al. (Biomed Papers 147:131, 2003), which is incorporated herein by reference in its entirety. The principles and general procedures of each of these methods are, moreover, known in the art. In a particular embodiment of the invention, real-time PCR is used to detect gene expression of iPSC markers.

Real-Time PCR

As taught herein, detection of ESSRB, NANOG, UTF1, endogenous Pou5f1 (also known as Oct4) or endogenous SOX2 gene expression may be used as a means to assess induced PSCs. Detection of these markers in generated iPSCs at similar levels as seen in established reference PSCs such as ESCs or validated iPSC lines, therefore, provides positive indicators or readouts for the present method for generating iPSCs from somatic cells.

A variety of protocols are available for measuring and/or detecting expression levels of polypeptides. Protocols for detecting polypeptide expression, such as, for example, immunohistochemistry and immunoblotting, are known in the art. These protocols are generally applicable to detecting ESSRB, NANOG or UTF1 polypeptides. Particular methods for detecting ESSRB, NANOG or UTF1 polypeptides are described in the Examples presented herein, as are reagents for performing such methods.

In general, immunoassays for polypeptides typically comprise contacting a sample, such as a population of cells (e.g., incubated in PSC inducing conditions) or lysates thereof in the presence of an antibody that specifically or selectively binds to a polypeptide in question, e.g., a detectably labeled antibody capable of identifying the particular polypeptide (e.g., NANOG) and detecting the bound antibody by any of a number of techniques well-known in the art (e.g., Western blot, ELISA, FACS).

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled antibody that selectively or specifically binds to the particular polypeptide (e.g., an iPSC marker). The solid phase support may then be washed with the buffer a second time to remove unbound antibody. The amount of bound label on a solid support may then be detected by conventional means.

More particularly, iPSC marker protein levels can be assessed by cell surface staining for SSEA1 and EpCAM; ELISA for UTF1, NANOG, and ESRRB; intracellular staining for UTF1, NANOG, and ESRRB; and Western Blot for UTF1, NANOG, and ESRRB. Indeed, in principle all exemplary PSC markers listed above with the exception of SSEA1 and CD9 should be detectable by ELISA, Western blot and intracellular staining.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Particular supports include polystyrene beads. Those skilled in the art will know many other suitable carriers for binding antibody or antigen, or will be able to ascertain the same by use of routine experimentation.

An antibody can be detectably labeled by linking same to an enzyme and using the labeled antibody in an enzyme immunoassay (EIA) (Voller, A., "The Enzyme Linked Immunosorbent Assay (ELISA)", 1978, *Diagnostic Horizons* 2:1, Microbiological Associates Quarterly Publication, Walkersville, Md.); Voller, A. et al., 1978, *J. Clin. Pathol.* 31: 507-520; Butler, J. E., 1981, *Meth. Enzymol.* 73:482; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme that is bound to the antibody reacts with an appropriate substrate, particularly a chromogenic substrate, in such a manner as to produce a chemical moiety detectable, for example, by spectrophotometric, fluorometric or by other visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect a polypeptide through the use of a radioimmunoassay (RIA). The radioactive isotope can be detected by such means as the use of a gamma counter or a scintillation counter or by autoradiography.

An antibody may also be labeled with a fluorescent compound. When the fluorescently labeled antibody is exposed to light of the proper wavelength, its presence can be detected due to fluorescence emission. Among the most commonly used fluorescent labeling compounds are fluorescein isothiocyanate, rhodamine, phycoerythrin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

An antibody can also be detectably labeled by coupling it to a chemiluminescent compound. The presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label an antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The basic molecular biology techniques used to practice the methods of the invention are well known in the art, and are described for example in Sambrook et al., 1989, *Molecular Cloning: A Laboratory Manual*, Cold Spring Harbor Laboratory, New York; Ausubel et al., 1988, *Current Protocols in Molecular Biology*, John Wiley & Sons, New York; and Ausubel et al., 2002, *Short Protocols in Molecular Biology*, John Wiley & Sons, New York).

Pharmaceutical Compositions

The present invention also provides pharmaceutical compositions. Such compositions comprise a therapeutically effective amount of an agent and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions will contain a therapeutically effective amount of the compound, preferably in purified form, together with a suitable amount of carrier so as to provide the form for proper administration to the subject. The formulation should suit the mode of administration.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of compounds described herein which will be effective in the treatment of a disease or disorder can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

In an embodiment, the iPSCs or specific somatic cell types derived from such iPSCs may be administered alone or in a composition to a subject in a systemic or a localized fashion. Systemic administration may, for example, be achieved via intravenous injection. Systemic administration could, for example, be used to advantage to repopulate a blood cell type in a subject in need thereof, such as, for example, a subject who has undergone radiation and/or chemotherapy to irradicate a blood cell cancer and is in need of reconstitution with respect to circulating blood cells and progenitors thereof Localized administration to a specific site or sites of an injury or missing tissue may, for example, be achieved via localized introduction or injection of the iPSCs or specific somatic cell types derived from such iPSCs to the specific site or sites in need thereof. Localized administration benefits from directed delivery of a maximized dose of iPSCs or specific somatic cell types derived from such iPSCs to the site/sites in need of repair and/or restoration. Accordingly, localized administration is particularly well suited to address localized injuries, such as, without limitation, those of a joint (e.g., a knee, elboe, ankle, wrist, shoulder, or hip), a muscle or muscle group, a bone, or an organ (e.g. liver or heart).

Transfection

As described herein and understood in the art, exogenous nucleic acids can be transferred into cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells can then be used as therapeutic agents and delivered to a subject.

In this embodiment, a nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Hu (2014, Stem Cells Development 23:1301-1315) and references cited therein provide a comprehensive overview of current technologies used for transfection in the context of iPSC formation. The entire content of each of Hu and the references cited therein is incorporated herein by reference in its entirety. Crispr/Cas9 technology is also envisioned for generating iPSCs. In a particular embodiment thereof, the endogenous reprogramming factor genes (OKSM) could be activated using CRISPR/Cas9 technology. See, for example, Gilbert et al. (2014, Cell 159:647-661), the entire content of which is incorporated herein by reference.

The resulting recombinant cells can be delivered to a subject by various methods known in the art. In a particular embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The number of cells envisioned for use depends on the desired effect, the condition of the subject, etc., and can be determined by one skilled in the art.

Cells into which a nucleic acid can be introduced for purposes of gene therapy encompass any desired available cell type, and include but are not limited to fibroblasts; hepatocytes; hepatoblasts; neuronal cells; immature blood cells such as granulocyte-macrophage progenitors (GMPs), common myeloid progenitors (CMPs), megkaryocyte-erythrocyte progenitors (MEPs), and multipotent lineage-negative Sca$^+$kit$^+$ (LSK) cells; blood cells such as T lymphocytes, B lymphocytes, monocytes, macrophages, neutrophils, eosinophils, megakaryocytes, and granulocytes; epithelial cells; endothelial cells; keratinocytes; and muscle cells. Such cells may be of any mammalian species, including without limitation: mice, rats, pigs, cats, dogs, horses, cows, camels, primates in general, and humans in particular. In a particular embodiment, the cell used for gene therapy is autologous to the subject that is treated.

Figure 5A:
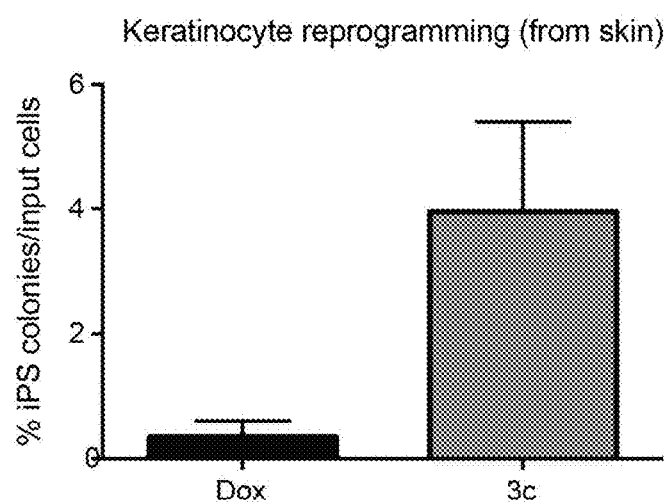
FIG. 5A-5B. Synergistic effects of 3c on the induction of pluripotent stem cells from keratinocytes and B cells in the context of exposure to exogenous reprogramming factors (OKSM). Reprogramming efficiency for (5A) keratinocytes isolated from skin and (5B) B lymphocytes isolated from spleen is shown. Briefly, B cells and keratinocytes were isolated from transgenic animals carrying a doxycycline (dox)-inducible cassette encoding OKSM and seeded at clonal density onto irradiated feeder cells into dox-containing reprogramming media plus/minus 3c compounds. Compounds were removed two weeks later and iPSC colonies scored based on established pluripotency markers another 4 days later. Experiments were done in duplicate.
Figure 5B:
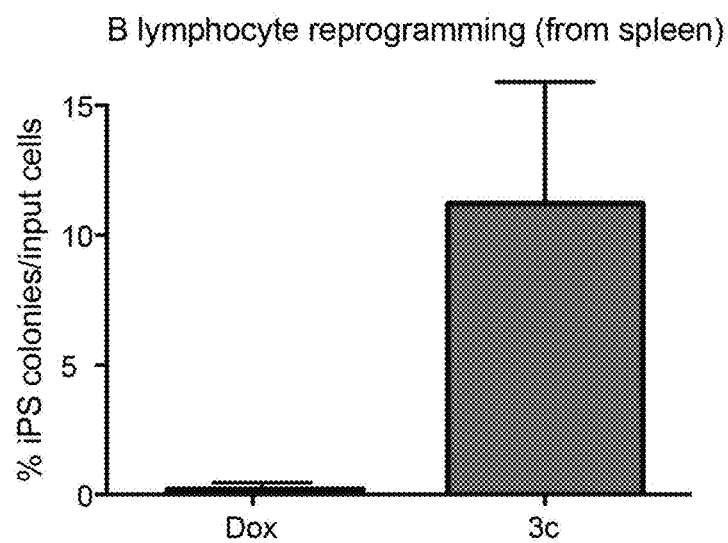

Further to the above, the 3c triple compound combination acted in a synergistic fashion to generate iPSCs from keratinocytes isolated from skin and B lymphocytes isolated from spleen. See, for example, FIG. 5. The 3c triple compound combination, moreover, acted in a synergistic fashion to generate iPSCs from human blood progenitor cells. See, for example, FIG. 13.

In another embodiment, the nucleic acid to be introduced for purposes of gene therapy may comprise an inducible promoter operably linked to the coding region, such that expression of the nucleic acid is controllable by adjusting the concentration of an appropriate inducer of transcription. Upon withdrawal of the appropriate inducer of transcription or inducing agent, the expression of the nucleic acid operably linked to the inducible promoter decreases and eventually ceases. Accordingly, inducible systems may be used to turn on and off expression responsive to the presence and/or concentration of the inducing agent. The nature of the inducing agent depends on the inducible system chosen for use. Exemplary inducible systems for use in methods described herein include those based on tetracycline-derivatives [see, for example, Gossen et al. (1993, Trends Biochem Sci 18:471-475)], estrogen receptor fusions [see, for example, Whitfield et al. (2015, Cold Spring Harbor Protoc 2015(3):227-234)], and optogenetics [see, for example, Yin et al. (2013, Pflugers Arch 465:397-408)], the entire content of each of which is incorporated herein by reference. Other inducible systems are described herein and known in the art.

Homogeneous Populations of Reprogramming Intermediates on Pathway to Becoming Mammalian iPSCs The novel methods of the present invention facilitate the generation of a homogeneous population of mammalian (e.g., human, mouse, or rat) reprogramming intermediates that are transitioning to become iPSCs, the population comprising about or at least 10-1,500 and more particularly, about or at least 10-1,000 homogeneous mammalian reprogramming intermediates, wherein the mammalian reprogramming intermediates express cellular markers of PSCs, such as, e.g., ESSRB, NANOG, UTF1, or endogenous SOX2. Indeed, a unique feature of reprogramming intermediates in 3c conditions relates to the structural/functional distinction that they activate expression of stringent pluripotency markers such as esrrb, utf1 and endogenous pou5f1/sox2 in a highly synchronized and homogeneous manner. Further to this point, the reprogramming intermediates generated in 3c conditions express each of esrrb, utf1 and endogenous pou5f1/sox2 rapidly in 3c conditions. This stands in marked contrast to reprogramming intermediates generated via "basal" reprogramming using standard reprogramming conditions.

Accordingly, the term "reprogramming intermediates" refers to cells that are still expressing exogenous reprogramming factors and are in transition from a somatic cell state to that of pluripotency.

The term "induced pluripotent stem cells" or "iPSCs" as used herein refers to stable endproducts of the reprogramming process that still comprise nucleic acid sequences encoding exogenous reprogramming factors, but no longer express the exogenous reprogramming factor proteins.

In a particular embodiment, methods described herein are used to generate approximately 100 iPSCs from a single fibroblast cell after 7 days in 3c conditions. For the purposes of comparison, it is noteworthy that iPSCs are undetectable if a single fibroblast cell has been incubated under standard reprogramming conditions for a week.

In another particular embodiment, methods described herein are used to generate approximately several hundred to equal to or greater than 1,000 iPSCs from a single blood progenitor cell after 7 days in 3c conditions. For the purposes of comparison, it is noteworthy that iPSCs are undetectable if a single blood progenitor cell has been incubated under standard reprogramming conditions for a week.

Unless defined otherwise, all technical and scientific terms used herein have the same meaning as commonly understood by one of ordinary skill in the art to which this invention belongs.

It is to be understood that this invention is not limited to particular assay methods, or test agents and experimental conditions described, as such methods and agents may vary. It is also to be understood that the terminology used herein is for the purpose of describing particular embodiments only, and is not intended to be limiting, since the scope of the present invention will be limited only the appended claims.

EXAMPLE I

Experimental Procedures
Mice

Derivation, handling and genotyping of reprogrammable mice (JAX011001) with the Oct4-GFP reporter were described previously (Stadtfeld et al., 2010). DsRed transgenic animals (Vintersten et al., 2004) were obtained from Jackson Laboratories (JAX006051).

Cell Culture and Reprogramming

MEFs (Stadtfeld et al., 2008) and hepatoblasts (Gailhouste, 2012) were isolated from E14.5 embryos and GMPs, CMPs, MEP and LSK cells from either fetal liver or adult bone marrow (Akashi et al., 2000). All cell types used for reprogramming experiments were heterozygous for the inducible OKSM cassette, Rosa26-rtTA and the Oct4-GFP reporter. MEFs were expanded in reduced-oxygen conditions (4%) and used at passages 1 or 2. For reprogramming, cells were seeded in ESC media (DMEM with 15% FBS, L-glutamin, penicillin-streptomycin, nonessential amino acids, β-mercaptoethanol and 1000 U/ml LIF) at the desired density on a layer of irradiated feeder cells in presence of 1 mg/ml doxycycline. If applicable, L-Ascorbic acid (50 ng/μl), CHIR99021 (3 μM), TGFβ RI Kinase Inhibitor II (250 nM) and PD032590 (0.75 μM) were added. For GMPs and other blood progenitors, cultures were supplemented with Flt3-ligand (10 ng/ml) and SCF (20 ng/ml) for the first three days of reprogramming. Media was replenished every two days. To facilitate detection of Oct4-GFP expression in nascent colonies by fluorescent microscopy, reprogramming experiments were conducted in ESC media prepared with FluoroBrite DMEM (Life Technologies) when required. To score factor-independent colonies, dox (and other compounds) were removed by washing cultures twice with PBS and then maintaining them in ESC media for at least three days before colonies were counted by fluorescence microscopy or after alkaline phosphatase staining (Vector Laboratories). For quantification of Oct4-GFP expression, cultures were harvested by trypsin digestion, stained with DAPI or 7-AAD to exclude dead cells, acquired on a LSRII cytometer (BD Biosciences) and analyzed with FlowJo software (Tree Star Inc.).

In other embodiments envisioned, the cells are homozygous or heterozygous for all three alleles (OKSM, rtTA, Oct4-GFP) in any combination and such combinations would yield comparable results. It is noteworthy that only two alleles (OKSM and rtTA) are required for drug-inducible reprogramming.

Immunofluorescence

Cells were fixed with paraformaldehyde, permeabilized and stained with primary antibodies against Oct4 (Santa Cruz, sc-8628), Nanog (Abcam, ab808992), Utf1 (Abcam, ab24273), Sall4 (Abcam, ab29112), Lin28 (Abcam, ab46020) and β-catenin (Sigma, C7207) followed by staining with appropriate secondary antibodies conjugated to either Alexa Fluor 555 or 647 (Invitrogen). Images were acquired with a Neo 5.5 cSMOS camera (Andor) and processed and analyzed using NIS-Elements and Adobe Photoshop.

Lentiviral Vectors

VSV-G pseudotyped lentiviral vectors were produced in 293T cells and concentrated by ultracentrifugation as described in detail before (Sommer et al., 2009). Transduction of MEFs ($3 \times 10^4$ cells) and blood progenitor cells ($1 \times 10^5$ cells) was carried out in presence of 5 μg/ml polybrene.

Microarray Analysis

For the study of reprogramming intermediates, cultures of reprogrammable MEFs at day 4 in presence of OKSM expression were harvested and stained with biotinylated anti-SSEA1 antibody (MC-480, eBioscience), followed by APC-conjugated Streptavidin and anti-APC microbeads (Milteny Biotec). SSEA1$^+$ cells were enriched to ~90% purity using MACS separation columns (Milteny Biotec) according to the manufacturer's instructions. Total RNA extracted with the miRNeasy mini kit (QIAGEN) with a RIN value >8 was subjected to transcriptional analyses with Affymetrix mouse genome 430 2.0 mRNA expression microarrays followed by bioinformatic analyses. This data can be accessed as record GSE59865 in NCBI's Gene Expression Omnibus. For the study of signaling pathways in starting cell populations expression values of transcripts characteristic for TGFβ (GO:0007179) and Wnt signaling (GO:0016055) were extracted from public datasets.

Cell Isolation and Culture

ESCs and iPSCs were cultured in basal ESC medium (DMEM with 15% FBS, L-Glutamine, penicillin-streptomycin, non-essential amino acids, 2-Mercaptoethanol and 1000 U/ml LIF) on irradiated feeder cells. MEFs were isolated by trypsin-digestion of midgestation (E14.5) embryos followed by culture in fibroblast medium (DMEM with 10% FBS, L-Glutamine, penicillin, streptomycin, non-essential amino acids and 2-Mercaptoethanol). Hepatoblasts were isolated by enzymatic digestion of E14.5 fetal liver with collagenase IV (Sigma) as previously described (Gailhouste, 2012) and FACS purified after staining with an antibody against E-cadherin (DECMA-1, eBiosciences). GMPs, CMPs, MEP and LSK cells were isolated from fetal liver of midgestion embryos or from adult bone marrow using FACS based on expression of a panel of lineage associated surface markers (B220, CD3, Ter119, Gr1 and CD127) and specific combinations of Sca-1, c-kit, CD34 and FcγRI expression (Akashi et al., 2000). Cells used for single cell seeding experiments were isolated from chimeric embryos obtained after diploid blastocyst injections with reprogrammable iPSCs harboring the DsRed transgene and seeded directly into 96-well plates. All sorting was done on either a FACSAria (BD Biosciences) or a Beckman Coulter MoFlo (Cytomation). A well was scored as successfully seeded if it contained at least a "mini cluster" of >1 DsRed$^+$ cells (demonstrating cell survival and ability to proliferate). Seeding efficiencies observed were 40-60% (for hepatoblasts and MEFs) and 70-90% (for GMPs).

Blastocyst Injection, Chimera Generation and Germline Transmission Assessment

Female BDF1 mice were superovulated by intraperitoneal injection of PMS and hCG and mated to BDF1 stud males as previously described (Eggan et al., 2001). Zygotes were isolated from females with a vaginal plug 24 hour after hCG injection. After in vitro culture for 3 days in KSOM media, blastocysts were identified, injected with iPSCs and transferred into pseudopregnant recipient females. Generated chimeras were back-crossed with C57BL/6 mice to assess germline transmission.

Viral Expression Plasmids

The following cDNAs were used for subcloning into the pHAGE-EF1a-IRES-tdTomato vector system (provided by Dr. Gustavo Mostoslaysky, Boston University): the catalytic domain of human TET1 (NM_030625.2; gift from Dr. Mamta Tahiliani, NYU School of Medicine); full-length human KDM6A (Dr. Iannis Aifantis, NYU School of Medicine); full length human KDM2B (NM_032590.4; Dr. Michele Pagano, NYU School of Medicine); full-length human S37A (degradation resistant) CTNNB1 (NM_001904.3; Dr. Claudio Basilico, NYU School of Medicine); full-length mouse Wdr5 (Dr. Iannis Aifantis, NYU School of Medicine), full-length mouse Ezh2 (Dr. Danny Reinberg, NYU School of Medicine) and full-length mouse Smarcc1 (NM_009211.2; Addgene plasmid 25856).

Transduction of Blood Progenitors Cells $1 \times 10^5$ Kit$^+$ cells purified from adult bone marrow with microbeads (Milteny Biotec) were mixed with 10-20 µl of concentrated virus and plated into one well of a U bottom 96 well plate in 200 µl OP9 medium supplemented with 20 ng/ml SCF, 10 ng/ml Flt, 10 ng/ml IL-3, 10 ng/ml TPO and 5 µg/ml polybrene. The plate was then centrifuged at 2000 rpm, 30° C. for 1.5 hours. The same procedure was repeated 12 hours later to increase the transduction efficiency.

Differential Expression Analysis

Pair-wise differential expression of MEFs, ESCs, GMPs and HEPs was assessed using a t-test and the resulting p-values were adjusted for multiple hypothesis testing as by the Benjamini & Hochberg procedure. The reported gene signatures are based on 1e-3 adjusted p-value and 1.5 fold-change cutoffs. For the d4-intermediates dataset, the present inventors also applied a 1.5 fold-change cutoff at 1% false discovery rate (FDR). FDR was assessed using the following methodology. Differential expression between pairs of samples was determined using a method that evaluates the significance of gene expression fold changes (Tu et al., 2002). Briefly, differential expression was assessed for every Affymetrix transcript probe between samples. As a preprocessing step, quantiles were normalized across samples and replicates, and subsequently fold changes were computed for each probe across the two replicates of each sample. The false discovery rate was computed by comparing the distribution of fold changes against the distribution of fold changes between replicates of the same sample. Public microarray data sets were obtained from the Gene Expression Omnibus (NCBI) for wild-type hepatoblasts (GSE7038 and GSE6966), MEFs (GSE25257, GSE16266, GSE10902 and GSE18286), GMPs (GSE35844, GSE21018, GSE27816 and GSE37301) and pluripotent cells (GSE34761 and GSE16925).

Gene Set Enrichment Analysis

For the functional enrichment analysis, MSigDB version 4.0 was used (Subramanian et al., 2005). The enrichment analysis consisted of computing p-values for the intersections between the gene list of interest α (up-regulated or down-regulated genes) and each gene set β in MSigDB (constrained in the set of differentially expressed genes). For each pair of gene sets α and β, the present inventors computed the probability (p-value) that the observed overlap between sets α and β is less than or equal to the overlap between set α and a randomly-chosen set of size equal to the size of set β. This probability was calculated by applying the cumulative density function of the hypergeometric distribution on the size of set α, the size of set β, the observed overlap between α and β, and the number of differentially expressed genes.

Statistical Analysis

Data was analyzed for statistically significant differences using a t-test, a one-way ANOVA or a Fisher's exact test where appropriate, using GraphPad Prism 6.0e.

Results

Synergism Between Small Molecule Compounds Allows Highly Efficient Reprogramming of Mouse Fibroblasts To study synergisms between signaling pathways during iPSC formation the present inventors focused on TGFβ and Wnt signaling since a role for these pathways in fibroblasts reprogramming has been documented and highly specific compounds targeting them are available. Specifically, the TGFβ antagonist ALK5 inhibitor II ("iAlk5") (Maherali and Hochedlinger, 2009) and the GSK3β antagonist CHIR99021 ("CHIR") (Li et al., 2009), which activates Wnt signaling by stabilizing β-catenin, were employed. In light of the importance of chromatin remodeling for iPSC formation, the present inventors also included ascorbic acid (AA), an enzymatic co-factor that facilitates fibroblast reprogramming (Esteban et al., 2010).

Figure 6A:
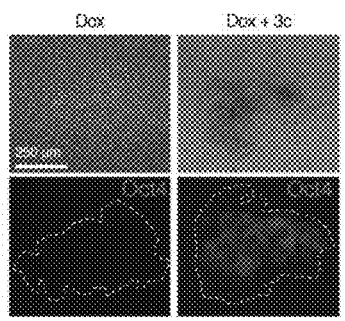
FIG. 6A-6F. Related to FIG. 1. (6A) Representative phase contrast and Oct4-GFP fluorescent images of MEF-derived colonies after 12 days in dox or 6 days in dox+3c. Dotted lines indicate colony borders. (6B) Experimental approach for the quantification of iPSC formation after single cell sorting of reprogrammable cells with the Oct4-GFP reporter and a ubiquitous DsRed transgene into 96 well plates. (6C) Representative immunofluorescence (IF) images of Nanog and Utf1 expression in MEF-derived colonies after six days of cultures in dox or dox+3c. (6D) Percent of colonies expressing the indicated pluripotency markers as measured by IF at day 6 under dox or dox+3c. Mean and range of two independent experiments with at least 40 colonies scored. (6E) Quantification of the number of cells in colonies (n=24 independent colonies) formed from single MEFs cultured for three days in basal ESC media, in dox alone or dox+3c. P values were calculated with one-way ANOVA. (6F) Image of an adult coat color chimera together with his germline offspring (red arrow) obtained upon blastocyst injection with a MEF-iPSC clone derived in 3c conditions.

The aforementioned compounds were tested using "reprogrammable MEFs" (Stadtfeld et al., 2010) engineered to express a doxycycline (dox)-inducible cassette encoding OKSM (Sommer et al., 2009) from a single defined genomic position and a GFP reporter from the endogenous Oct4 locus, whose expression is a hallmark of the pluripotent state. The present inventors initially administered dox and different combinations of compounds for six days to reprogrammable MEFs seeded in bulk. This was followed by three days of culture in unsupplemented mouse embryonic stem cell (ESC) media to select for fully reprogrammed cells (FIG. 1A). In dox alone, these conditions were insufficient for Oct4 reactivation or to generate stable ESC-like colonies (FIG. 1B,C and FIG. 6A) but each of the three compounds individually allowed small numbers of dox-independent colonies to emerge, with efficiencies ranging from 0.5% (CHIR) to about 2% (AA and iAlk5) of input cells (FIG. 1B). The dual compound combinations of CHIR plus AA and CHIR plus iAlk5 slightly elevated colony numbers (5%) while the combination of iAlk5 and AA led to a more dramatic increase (21%) (FIG. 1B). This synergistic effect was most pronounced when using all three chemicals together, frequently resulting in Oct4 reactivation at Day 6 (FIG. 6A) and stable dox-independent iPSC colonies at an average efficiency of 41% (FIGS. 1B,C). For simplicity, the combination of AA, iAlk5 and CHIR is referred to as "3c" hereinafter.

Additional pluripotency loci that may be used in conjunction with the present methods include, without limitation, the Zfp42 (Rex1), Fbx15 (Fbxo15), Esrrb, Sox2, Otx2 and Lefty2 loci. Additional reporter genes that may be used in conjunction with the present methods include, without limitation, the tdTomato, YFP, Venus, mCherry, and RFP genes.

Figure 6B:
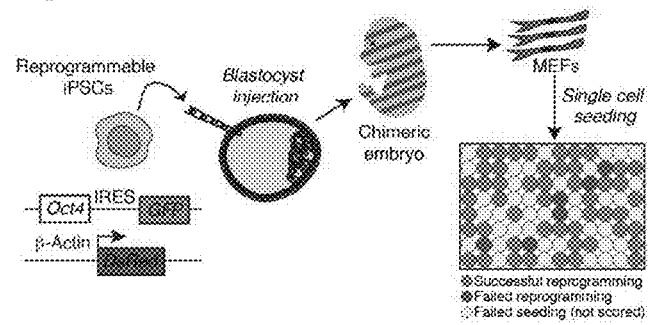

Timed withdrawal experiments revealed that a minimum of three days of OKSM expression was sufficient for a small subset of MEFs to enter a self-sustained pluripotent state in 3c. This was followed by a dramatic (~50 fold) increase in colony numbers between days three and five (FIG. 1D), after which colony numbers plateaued. These observations indicate exceptionally rapid and synchronized acquisition of pluripotency, which is in stark contrast to the slow and sporadic reprogramming observed in dox only (FIG. 1D). To accurately determine reprogramming efficiencies, single cell seeding experiments were conducted with reprogrammable MEFs that harbor a ubiquitously expressed red-fluorescent DsRed transgene (Vintersten et al., 2004) (FIG. 6B), thus excluding cells that fail to seed and reducing the risk of scoring satellites colonies (Smith et al., 2010). This stringent assay showed that seven days in dox+3c was sufficient for >80% of MEFs to give rise to colonies that maintained ESC-like morphology in the absence of exogenous OKSM expression (FIG. 1E). This correlated with the reactivation of Oct4 in the comparatively short time window between day 4 and day 7 in most colonies in dox+3c (FIG. 1F). In contrast, less than 2% of MEFs acquired dox-independence after 12 days of OKSM expression in dox only with Oct4 reactivation occurring late and in rare colonies (FIG. 1E,F).

Figure 6C:
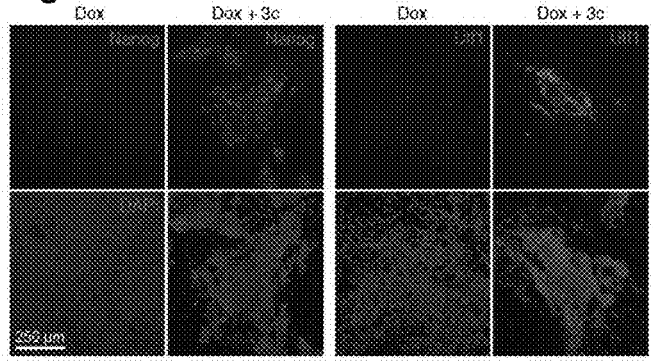
Figure 6D:
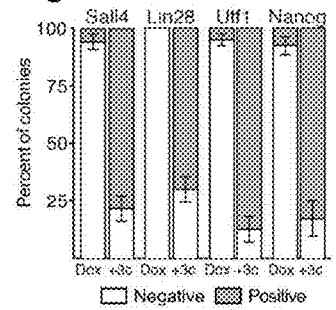
Figure 6E:
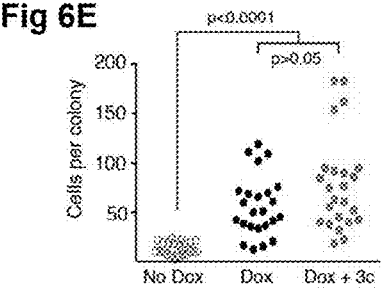

At the molecular level, the synergistic effect exerted by 3c on iPSC formation was accompanied by the upregulation of large numbers of genes including ESC-associated transcripts such as Tet1, Epcam, Eras and Nanog in day 4 reprogramming intermediates (Brambrink et al., 2008; Stadtfeld et al., 2008), which was not seen with individual compounds (FIG. 1G,H). GO analysis supported the conclusion that stem cell specific loci were only activated in the presence of all three compounds while individual chemicals facilitated the silencing of specific aspects of the somatic program, such as collagen synthesis (by iAlk5) and mesodermal differentiation potential (by AA) (Supplemental Table S1). Immunofluorescence confirmed accelerated reactivation of pluripotency loci such as Nanog, Utf1, Lin28 and Sall4, whose protein products were detectable in the majority of nascent colonies at day 6 in dox+3c (FIG. 6C,D). Together, these observations suggest a strong synergism between 3c compounds and reprogramming factors that allows reactivation of pluripotency loci that remain refractory in dox only conditions or in presence of individual compounds. Colonies that emerged in dox+3c and in dox alone contained similar numbers of cells. An accelerated cell cycle therefore does not seem to be specifically associated with the dramatically increased reprogramming efficiency (FIG. 6E).

TABLE S1

Selected categories from gene ontology analysis of day 4 intermediates

| | CATEGORY-ID | GENES-IN-CATEGORY | Q-VALUE | GENES | CATEGORY-DESCRIPTION |
|---|---|---|---|---|---|
| AA-specific (Down) | GO:0001501 | 81 | 0.00000 | 8 | skeletal development |
| | GO:0007507 | 180 | 0.00089 | 10 | heart development |
| AA-specific (Up) | GO:0005923 | 103 | 0.00000 | 7 | tight junction |
| CHIR-specific (Down) | GO:0005615 | 786 | 0.00000 | 10 | extracellular space |
| | GO:0006954 | 199 | 0.03100 | 5 | inflammatory response |
| CHIR-specific (Up) | GO:0043565 | 676 | 0.00000 | 5 | sequence-specific DNA binding |
| iAlk5-specific (Down) | GO:0005581 | 79 | 0.00000 | 4 | collagen |
| | GO:0008360 | 89 | 0.02100 | 4 | regulation of cell shape |
| | GO:0001569 | 36 | 0.02100 | 3 | patterning of blood vessels |
| iAlk5-specific (Up) | GO:0045668 | 35 | 0.00000 | 5 | negative regulation of osteoblast differentiation |
| | GO:0048712 | 13 | 0.02000 | 3 | negative regulation of astrocyte differentiation |
| | GO:0045893 | 509 | 0.02900 | 10 | positive regulation of transcription, DNA-dependent |
| 3c-specific (Down) | GO:0001938 | 45 | 0.00653 | 5 | positive regulation of endothelial cell proliferation |
| | GO:0045766 | 71 | 0.00653 | 6 | positive regulation of angiogenesis |
| | GO:0005581 | 79 | 0.00000 | 7 | collagen |

TABLE S1-continued

Selected categories from gene ontology analysis of day 4 intermediates

| | CATEGORY-ID | GENES-IN-CATEGORY | Q-VALUE | GENES | CATEGORY-DESCRIPTION |
|---|---|---|---|---|---|
| 3c-specific (Up) | GO:0001829 | 15 | 0.00000 | 4 | trophectodermal cell differentiation |
| | GO:0019827 | 30 | 0.00100 | 4 | stem cell maintenance |
| | GO:0042074 | 13 | 0.00900 | 3 | cell migration involved in gastrulation |

Figure 6F:
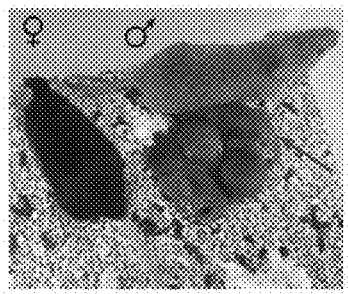

Clonal iPSC lines derived in the presence of 3c yielded chimeras with germline transmission (FIG. 6F and Supplemental Table S2). This demonstrates that the enhanced reprogramming kinetics do not come at the expense of impaired functional properties of derivative pluripotent cell lines.

TABLE S2

2n blastocyst injection

| iPS Line | Blasts transferred | Pups Born | Pups Survived | Chimeric Pups | Germ Line Transmission |
|---|---|---|---|---|---|
| MEF #1 | 10 | 0 | 0 | 0 | |
| MEF #2 | 10 | 5 | 5 | 4 | Yes |
| GMP #1 | 43 | 31 | 18 | 13 | Not Determined |
| GMP #2 | 35 | 20 | 11 | 4 | Not Determined |
| Hep #1 | 34 | 14 | 11 | 9 | Not Determined |
| Hep #2 | 44 | 10 | 9 | 3 | Not Determined |

Synchronous Induction of Pluripotency in Somatic Progenitor Cell Populations

Figure 7A:
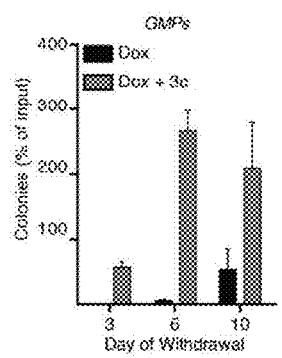
FIG. 7A-7H. Related to FIG. 2. (7A) Percentage of dox-independent colonies after culture of 200 reprogrammable GMPs for the indicated time in dox or dox+3c. (7B) Quantification of colonies derived from individual GMPs and MEFs that express Oct4 in a homogenous or heterogeneous manner or are negative after six days of culture in dox or dox+3c. Mean and range of two independent experiments with at least 40 colonies scored. (7C) Representative FACS plots for Oct4-GFP expression in clonal GMP-derived colonies after six days. (7D) Quantification of Oct4-GFP⁺ and Oct4-GFP⁻ cells (mean±standard deviation) in colonies derived from individual GMPs after six days of culture in dox (n=11 clonal colonies) or dox+3c (n=15 clonal colonies). (7E) Representative images of Nanog, Utf1 and Oct4-GFP expression in GMP-derived colonies cultured for six days in dox only. (7F) Percentage of dox-independent Oct4-GFP⁺ colonies formed upon culture of 100 reprogrammable hepatoblasts for the indicated time in either dox or dox+3c, followed by three days of culture in basal ESC media. Error bars indicate range of two independent experiments. (7G) Representative images of Lin28 and Nanog expression in hepatoblast-derived colonies at day 5 of reprogramming. (7H) Representative quantification of Oct4-GFP⁺ expression in colonies derived from individual hepatoblasts at day 5 of reprogramming.

Results presented herein show that combined Wnt activation and TGFβ inhibition in the presence of AA greatly facilitates the induction of pluripotency by OKSM in MEFs. The present inventors next sought to investigate whether 3c compounds can also enhance the reprogramming of somatic progenitor cells. Upon bulk culture of purified granulocyte-macrophage progenitors (GMPs), an immature blood cell type previously reported to yield iPSCs at efficiencies up to 30% after two weeks of OKSM expression (Eminli et al., 2009), the present inventors obtained dox-independent colonies at numbers corresponding to about 50% of input cells after three days in dox+3c (FIG. 7A). After six days—when the present inventors observed factor-independent colonies in dox only conditions at about 5% efficiency—colony numbers in the presence of 3c had further increased and exceeded the number of input GMPs, suggesting a propensity to generate satellite colonies.

Figure 7B:
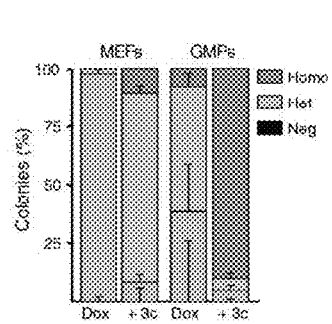
Figure 7C:
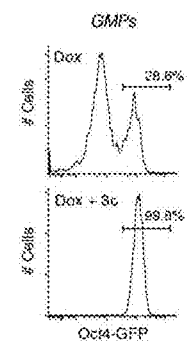
Figure 7D:
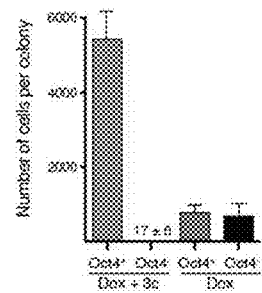
Figure 7E:
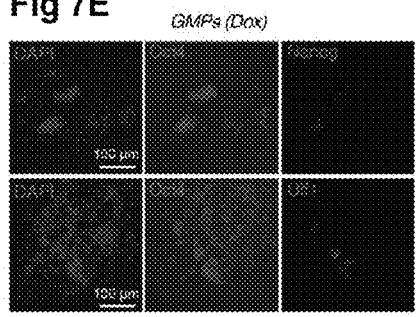

Importantly, single cell seeding of DsRed transgenic GMPs confirmed reprogramming efficiency of >95% in dox+3c (FIG. 7B). These experiments also revealed that the overall percentage of colonies containing Oct4-GFP$^+$ cells was similarly high with GMPs and MEFs in dox+3c (FIG. 7B). However, while almost all nascent GMP-iPSCs in the presence of 3c expressed endogenous Oct4 in a homogenous manner, MEFs in 3c (as well as GMPs in the absence of compound) represented a heterogeneous mixture of Oct4-GFP$^+$ and Oct4-GFP$^-$cells (FIG. 2A and FIG. 7B). Quantification by flow cytometry confirmed this striking difference and documented an average GFP-labeling index of >95% in the presence of 3c but of only about 40% in the absence of 3c (FIG. 2B and FIG. 7C). Time course analyses of clonal GMP cultures revealed that colonies with a GFP labeling index of greater than 90% appeared as early as day 3 in dox+3c and frequently encompassed all nascent colonies by day 6 (FIG. 2C). At this time, reprogramming cultures initiated with single GMPs in the presence of compounds on average contained over 5000 Oct4-GFP$^+$ cells and only negligible numbers of GMP-derived Oct4-GFP$^-$ cells (FIG. 7D). The pluripotency markers Nanog, Utf1, Lin28 and Sall4 were also expressed homogenously by the majority of colonies obtained after four days of culture in dox+3c (FIG. 2D, E). These results demonstrate that 3c conditions allow the vast majority of GMPs to acquire pluripotency in a highly synchronous manner upon OKSM expression. In contrast, the frequency of colonies with an Oct4-GFP labeling index greater than 90% in dox only remained below 10% (FIG. 2C) and the present inventors never observed GMP-derived colonies that did not contain cells that failed to reactivate Oct4 (FIG. 2B and FIG. 7D).

Figure 7F:
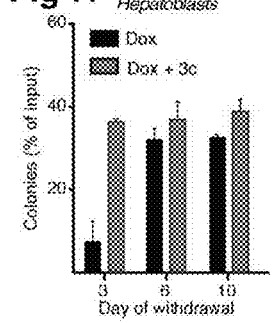
Figure 7G:
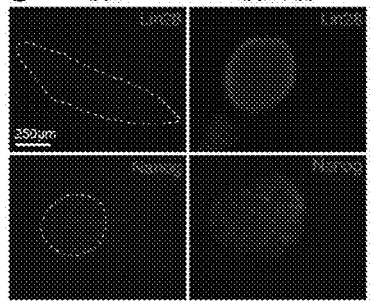
Figure 7H:
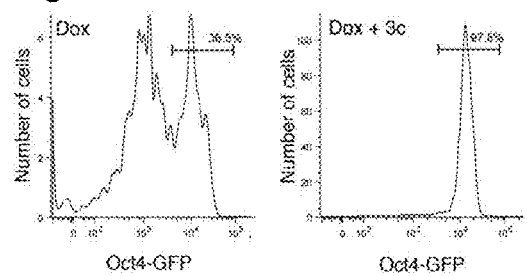

Timed dox withdrawal experiments were also performed with reprogrammable hepatoblasts, an endodermal progenitor cell unrelated to blood progenitors or MEFs that can be prospectively isolated by flow cytometry (Gailhouste, 2012). Rapid emergence of dox-independent colonies was observed upon culture of hepatoblasts in dox+3c, but not in dox only (FIG. 7F). Similar to GMPs, in the presence of 3c, the majority of cells within nascent hepatoblast-derived colonies expressed Oct4, Lin28 and Nanog (FIG. 2F and FIGS. 7G,H). Quantification after single cell seeding showed Oct4 expression in 95% of hepatoblast-derived colonies, with about 80% of them expressing this locus in a homogenous manner (FIG. 2G). Stable iPSC lines derived from GMPs and hepatoblasts yielded postnatal chimeras upon blastocyst injection (FIG. 2H and Supplemental Table S2). Together, these observations show that 3c reprogramming in both hepatoblasts and GMPs results in rapid and homogenous reactivation of ESC-specific loci, which is strikingly different from the stochastic reprogramming response normally associated with iPSC formation.

Specific Requirements of TGFβ and Wnt Signaling Modulation for Progenitor Cell Reprogramming MEF experiments presented herein revealed a strong synergism between AA and TGFβ inhibition and maximal reprogramming efficiencies upon further addition of CHIR (see FIG. 1B). The present inventors therefore asked whether GMPs and hepatoblasts have similar requirements for signaling pathway modulation and determined the efficiencies of iPSC formation upon reprogramming in presence of only AA, CHIR or iAlk5 compared to 3c.

Figure 8A:
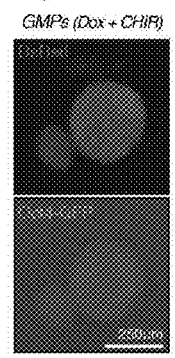
FIG. 8A-8G. Related to FIG. 3. (8A) Fluorescence images of DsRed and Oct4-GFP expression in a representative GMP-derived colony derived upon culture in dox+CHIR for six days. (8B) Percentage of Oct4-GFP⁺ cells in successfully reprogramming colonies after single cell seeding of GMPs in dox+CHIR or dox+3c, respectively (n=10 clonal colonies for each condition). (8C) AP staining of dox-independent colonies derived from LSK, GMP, MEP and CMPs in dox, dox+CHIR or dox+3c after six days of culture. (8D) Percentage of Oct4-GFP⁺ cells in colonies obtained after single cell seeding of hepatoblasts and culture under the indicated conditions for six days (n=10 clonal colonies). (8E) IF images of β-catenin staining in cells derived from GMPs cultured under dox or dox+CHIR for two days. White arrows highlight representative cells positive for β-catenin expression. (8F) Representative flow cytometry plots of Oct4-GFP expression in MEFs transduced with either empty or β-catenin virus and cultured under the indicated conditions for six days. (8G) AP staining of dox-independent colonies, derived after treating MEFs as outlined in panel 8F. Input=500 cells.
Figure 8B:
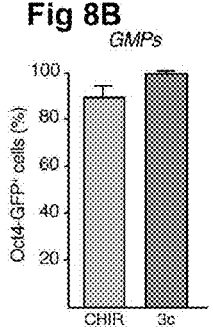
Figure 8C:
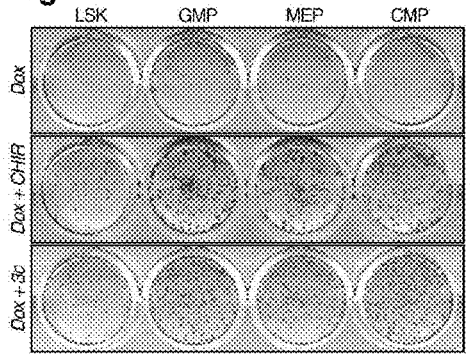

Strikingly, for GMPs supplementation of reprogramming media with CHIR alone allowed the formation of similar numbers of dox-independent colonies after six days of OKSM expression as with 3c (FIG. 3A,B). In contrast, colony numbers decreased 5-10 fold when using only AA or iAlk5 (FIG. 3B). By fluorescence microscopy, "CHIR only" colonies derived from single seeded GMPs showed homogenous Oct4 reactivation (FIG. 8A) and quantification by flow cytometry confirmed a GFP labeling index of over 90% (FIG. 8B). Of note, common myeloid progenitors (CMPs), megakaryocyte-erythrocyte progenitors (MEPs) and multipotent lineage-negative Sca1$^+$Kit$^+$ (LSK) cells also formed iPSCs with similar efficiencies in dox+CHIR and dox+3c, suggesting that a strong requirement for Wnt signaling activation is a common feature of blood progenitor cell reprogramming (FIG. 8C).

Figure 8D:
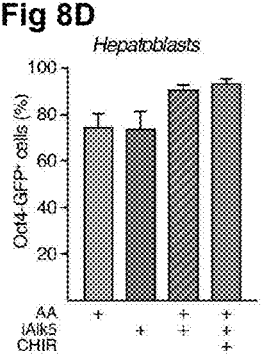

Other than for GMPs, CHIR had little beneficial effect on the number of iPSC colonies obtained from hepatoblasts (FIG. 3C). In contrast, these cells yielded dox-independent colonies efficiently in the presence of either iAlk5 or AA alone, reaching 60-80% of the numbers seen with 3c (FIG. 3C). Accordingly, both of these compounds facilitated synchronous reactivation of the Oct4 locus with their combination being equally efficient to 3c (FIG. 8D).

Figure 8E:
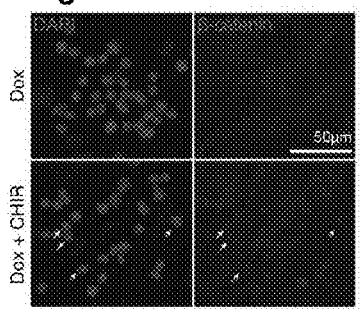
Figure 8F:
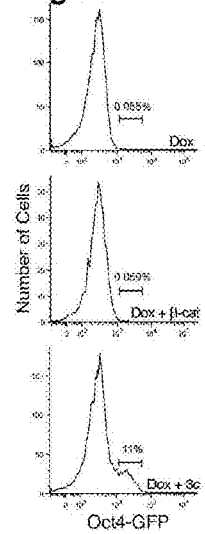
Figure 8G:
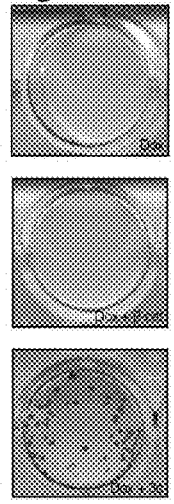

To investigate the reasons for these cell type specific differences, the present inventors studied the expression of TGFβ and Wnt signature genes in MEFs, GMPs and hepatoblasts. This revealed pronounced differences, with GMPs exhibiting significantly lower levels of gene products associated with both signaling pathways than hepatoblasts and MEFs (FIG. 3D). Among the differentially expressed genes were many core pathway components such as Tgfbr2 and different ligands (for TGFβ and Apc, Fzd1, Fzd2 and Ctnnb1 (for Wnt). Since Ctnnb1, also known as β-catenin, is an important mediator of canonical Wnt signaling (Nelson and Nusse, 2004), its role was further investigated. At the protein level, β-catenin rapidly accumulated in purified GMPs cultured in CHIR but not dox only (FIG. 8E), consistent with a role in the rapid reprogramming response. Indeed, lentiviral introduction of a stabilized variant of β-catenin (Rubinfeld et al., 1997) into blood progenitor cells resulted in efficient reactivation of Oct4 in presence of dox alone, which was indistinguishable from the degree of Oct4 reactivation seen with empty virus transduced cells reprogrammed in presence of 3c (FIG. 3E). Similar numbers of dox-independent colonies were also observed with β-catenin-transduced blood progenitors in dox alone and control cells in dox+3c, while no such colonies were seen with control cells in dox only (FIGS. 3F,G). This demonstrates that expression of β-catenin accelerates the OKSM-driven acquisition of pluripotency with similar efficiency to that of 3c. Ectopic β-catenin expression in MEFs undergoing reprogramming in dox alone did not result in early activation of Oct4-GFP or increased colony numbers (FIG. 8F,G). Together, these observations reveal that different cell types require specific signaling pathway modulations for rapid and efficient reprogramming and suggest that β-catenin-mediated Wnt activation is a major facilitator of blood progenitor cell reprogramming.

Facilitation of Synchronous Reprogramming in Fibroblasts

The results described above provide a rationale for the specific requirements of MEFs, GMPs and hepatoblasts for TGFβ and Wnt modulation during reprogramming. At the same time they suggest the existence of additional molecular differences between GMPs and MEFs that facilitate rapid and synchronous iPSC formation from the former. The present inventors hypothesized that these differences might encompass other signaling pathways and/or proteins involved in the epigenetic remodeling necessary for reprogramming to pluripotency and subjected the starting cell populations to additional rounds of bioinformatic analyses.

As shown in FIG. 9A, with this approach the present inventors identified MAP kinase signaling as significantly more active in MEFs than in GMPs. The present inventors therefore reprogrammed MEFs in reprogramming media supplemented with 3c and PD0325901, a specific inhibitor of mitogen-activated kinase kinases 1 and 2 that together with CHIR has been reported to facilitate the conversion of pre-iPSCs into iPSCs (Silva et al., 2008). Reprogramming in such 3 cM conditions did not affect the percentage of colonies that contained Oct4$^+$ cells compared to 3c, but nascent 3 cM colonies exhibited a more ESC-like morphology and significantly more homogenous expression of Oct4-GFP. (FIG. 4A and FIG. 9B). Nevertheless, the majority of colonies in dox+3 cM continued to contain cells that failed to reactivate Oct4, suggesting the existence of additional reprogramming barriers in MEFs.

Intriguingly, the present inventors found that many known epigenetic facilitators of iPSC formation (Apostolou and Hochedlinger, 2013; Papp and Plath, 2013) are expressed at higher levels in GMPs than in MEFs (FIG. 4B and Supplemental Table S3). A gain-of-function approach was therefore used to assess if any of these enzymes might elicit a reprogramming response in MEFs that is similar to GMPs and the present inventors cloned factors that represent different chromatin-modifying activities into lentiviral expression constructs. The present inventors chose Kdm2b (a H3K36me2 demethylase) (Wang et al., 2011), Kdm6a (a histone H3K27me3 demethylase) (Mansour et al., 2012), Wdr5 (a histone methyltransferase complex component) (Ang et al., 2011), Ezh2 (a component of polycomb repressive complex 2) (Onder et al., 2012), Smarcc1 (an ATP-dependent chromatin remodeling complex component) (Singhal et al., 2010) and the catalytic domain of the methylcytosine dehydrogenase Tet1, which is functionally equivalent to the catalytic domains of Tet2 and Tet3 (Hu et al., 2014). When culturing reprogrammable MEFs transduced with these vectors in dox+3c, the present inventors observed a strong and highly significant increase in the number of Oct4-GFP$^+$ cells with Kdm2b and a more modest response with Smarcc1 (FIG. 4C). A positive effect on Oct4 reactivation with any of the other factors (FIG. 4C) was not observed, suggesting that H3K36me2 demethylation, but not the other tested enzymatic activities are rate-limiting during 3c reprogramming. Ectopic expression of Kdm2b also shortened the time of dox exposure required for MEFs to enter a self-sustained pluripotent state (FIGS. 9C,D). Introduction of Kdm2b into MEFs cultured in reprogramming media supplemented with 3 cM resulted in Oct4 reactivation in about 80% of day 8 intermediates, suggesting synergism between this enzyme and MAP kinase inhibition (FIG. 4D). The present inventors also observed homogenous reactivation of Oct4, Sall4 and Nanog in the majority—about 70%—of nascent colonies in Kdm2b+3 cM conditions (FIG. 4E and FIG. 9E). Together, these results are consistent with the notion that reduced MAP kinase activity and elevated expression of specific pluripotency-associated epigenetic regulators contribute to the unique reprogramming response observed in GMPs, which in part can be established in MEFs.

TABLE S3

Differentially expressed epigenetic regulators in GMPs and MEFs

| Gene | Probe | log2 Expr (GMP - MEF) | qVal | log2 Expr (iPS/ES - MEF) |
|---|---|---|---|---|
| Cbx5 | 1421933_at | 2.08 | 0.0023 | 0.16 |
| Chd1 | 1431166_at | 2.70 | 0.0000 | 1.02 |
| Chd1 | 1457473_at | 1.85 | 0.0039 | 0.28 |
| Chd1 | 1450077_at | 1.78 | 0.0000 | 1.01 |
| Dot1l | 1457268_at | 1.34 | 0.0065 | 1.29 |
| Ezh2 | 1416544_at | 2.01 | 0.0000 | 2.73 |
| H2afy | 1424572_a_at | 2.16 | 0.0001 | 0.50 |
| Kdm2b | 1459861_s_at | 2.10 | 0.0002 | 1.97 |
| Kdm2b | 1452198_at | 1.89 | 0.0000 | 2.05 |
| Kdm3b | 1428320_at | 1.59 | 0.0000 | 0.64 |

TABLE S3-continued

Differentially expressed epigenetic regulators in GMPs and MEFs

| Gene | Probe | log2 Expr (GMP - MEF) | qVal | log2 Expr (iPS/ES - MEF) |
|---|---|---|---|---|
| Kdm3b | 1458417_at | 1.17 | 0.0063 | 1.54 |
| Kdm6a | 1445198_at | 2.23 | 0.0367 | 0.99 |
| Kdm6a | 1427672_a_at | 1.44 | 0.0002 | 0.81 |
| Parp1 | 1435368_a_at | 2.78 | 0.0000 | 2.52 |
| Parp1 | 1443573_at | 2.40 | 0.0001 | 1.42 |
| Smarcc1 | 1459824_at | 1.69 | 0.0000 | −0.27 |
| Smarcc1 | 1423416_at | 1.31 | 0.0000 | 1.22 |
| Suv39h2 | 1433996_at | 2.60 | 0.0005 | 1.31 |
| Suv39h2 | 1422979_at | 2.06 | 0.0018 | 2.32 |
| Suv39h2 | 1436561_at | 2.05 | 0.0004 | 1.01 |
| Tet1 | 1455425_at | 3.12 | 0.0000 | 6.57 |
| Tet1 | 1429448_s_at | 1.61 | 0.0145 | 5.63 |
| Tet1 | 1419897_at | 1.43 | 0.0306 | 1.46 |
| Tet2 | 1455300_at | 2.36 | 0.0002 | 2.43 |
| Tet2 | 1438781_at | 2.10 | 0.0007 | 3.10 |
| Wdr5 | 1416581_at | 1.69 | 0.0000 | 2.23 |
| Ehmt2 | 1460692_at | −1.37 | 0.0190 | 0.45 |
| Ehmt2 | 1426888_at | −3.29 | 0.0013 | 1.15 |
| Mbd3 | 1417728_at | −1.31 | 0.0002 | 0.32 |

Discussion

As described herein, the present inventors used a controlled genetic system to investigate to what extent the combinatorial modulation of TGFβ and Wnt signaling together with the enzymatic co-factor ascorbic acid ("3c conditions") can facilitate iPSC derivation from specific somatic cell types. While these compounds individually have been reported to moderately facilitate MEF reprogramming, the present results demonstrate a strong synergism among these compounds, which was previously not appreciated. By extending the present studies to hepatoblasts and blood progenitor cells, the present inventors were able to identify cell type-specific requirements for highly efficient and synchronized reprogramming to pluripotency. Importantly, for each of these cell types, the present inventors achieved reprogramming efficiencies of 80% and greater after less than a week of OKSM expression, which are among the highest efficiencies reported to date. This suggests that a chromatin state allowing OKSM to engage with appropriate target genes (Soufi et al., 2012) is quickly established during 3c reprogramming. The early upregulation of ESC-specific genes, which are normally subject to strict silencing mechanisms such as DNA methylation in somatic cells (Papp and Plath, 2013), supports this conclusion. Whether 3c compounds modulate the activity of molecules previously implicated in synchronized iPSC reprogramming responses such as Mbd3 (Rais et al., 2013) and Tet2 (Di Stefano et al., 2014; Doege et al., 2012) warrants further investigation.

Of the somatic cells included in the present study, MEFs revealed the most complex requirements for signaling pathway modulation and allowed highly efficient iPSC formation only in presence of all three compounds. In contrast, hepatoblast reprogramming was greatly facilitated by TGFβ inhibition alone, while GMPs required only Wnt activation—either by GSKβ inhibition or most strikingly by enforced expression of β-catenin—to rapidly reactivate pluripotency loci and to enter a pluripotent state. These cell type-specific requirements are reflected in the relative strength of TGFβ and Wnt signaling in the starting cell populations, suggesting a way to identify prospectively somatic cell types amenable to factor-mediated reprogramming. The observation that AA, a co-factor of chromatin-modifying enzymes, did not significantly enhance iPSC formation from blood progenitor cells indicates that an epigenetic state favorable to reprogramming might preexist in these cells. However, the present inventors cannot rule out that AA modulates GMP reprogramming in a way not measured by assays presented herein.

The present inventors observed marked differences between fibroblasts and somatic progenitor cells with respect to the synchronicity of reprogramming, defined as the percentage of cells within an emerging colony that expresses ESC-specific genes. Thus, while GMPs and also hepatoblasts rapidly and predominantly gave rise to colonies containing exclusively cells that had reactivated endogenous pluripotency loci, the present inventors only infrequently and later during reprogramming observed nascent MEF-iPSCs with these characteristics (see the model in FIG. 4F). This further supports the notion that specific molecular features "prime" progenitor cells for efficient reprogramming. Indeed, reducing MAP kinase signaling and elevating the levels of the histone demethylase Kdm2b—two intrinsic features of GMPs identified herein—facilitated the synchronous reactivation of pluripotency loci in MEFs. This is in agreement with the ability of Kdm2b to activate genes during early phases of iPSC formation (Liang et al., 2012) and suggests that rapid removal of epigenetic barriers by this enzyme in GMPs might be involved in the remarkable reprogramming response of these cells. It will be interesting to study how OKSM factors, chromatin modulators and β-catenin, an interaction partner of pluripotency factors (Kelly et al., 2011), cooperate to achieve rapid iPSC formation.

Our observation that GMPs can readily acquire pluripotency upon OKSM expression is reminiscent of a recent report that describes privileged reprogramming properties of a fast cycling subset within this progenitor cell population (Guo et al., 2014). While results presented herein do not exclude a role of fast cell cycle transition in synchronous GMP reprogramming, they imply that the molecular mechanisms underlying this phenomenon are complex and involve additional cellular features. The synchronous reactivation of pluripotency loci in almost all GMP-derived iPSC colonies suggests that 3c conditions override any heterogeneity that might exist within the GMP pool.

The high colony formation efficiency of close to 100% in less than a week, the rapid and homogenous reactivation of core pluripotency loci and the virtual absence of non-reprogrammed cells upon OKSM expression in blood progenitors in 3c resembles reprogramming kinetics reported after Mbd3 deletion in somatic cells (Rais et al., 2013). This suggests that at least some adult cell types can achieve so-called nonstochastic or deterministic reprogramming upon more subtle experimental modulation than the genetic interference with essential endogenous genes (see Model in FIG. 4F). Collectively, results presented herein define cell type-specific requirements for highly efficient and synchronous iPSC formation from different somatic cells by combined modulation of signaling pathways and chromatin modifiers. This provides a refined framework for the further exploration of the mechanisms underlying the erasure of the somatic state and the induction of pluripotency.

While certain of the particular embodiments of the present invention have been described and specifically exemplified above, it is not intended that the invention be limited to such embodiments. Various modifications may be made thereto without departing from the scope and spirit of the present invention, as set forth in the following claims.

REFERENCES

Akashi, K., Traver, D., Miyamoto, T., and Weissman, I. L. (2000). A clonogenic common myeloid progenitor that gives rise to all myeloid lineages. Nature 404, 193-197.

Ang, Y. S., Tsai, S. Y., Lee, D. F., Monk, J., Su, J., Ratnakumar, K., Ding, J., Ge, Y., Darr, H., Chang, B., et al. (2011). Wdr5 mediates self-renewal and reprogramming via the embryonic stem cell core transcriptional network. Cell 145, 183-197.

Apostolou, E., and Hochedlinger, K. (2013). Chromatin dynamics during cellular reprogramming. Nature 502, 462-471.

Brambrink, T., Foreman, R., Welstead, G. G., Lengner, C. J., Wernig, M., Suh, H., and Jaenisch, R. (2008). Sequential expression of pluripotency markers during direct reprogramming of mouse somatic cells. Cell stem cell 2, 151-159.

Buganim, Y., Faddah, D. A., Cheng, A. W., Itskovich, E., Markoulaki, S., Ganz, K., Klemm, S. L., van Oudenaarden, A., and Jaenisch, R. (2012). Single-cell expression analyses during cellular reprogramming reveal an early stochastic and a late hierarchic phase. Cell 150, 1209-1222.

Cherry, A. B., and Daley, G. Q. (2013). Reprogrammed cells for disease modeling and regenerative medicine. Annual review of medicine 64, 277-290.

Di Stefano, B., Sardina, J. L., van Oevelen, C., Collombet, S., Kallin, E. M., Vicent, G. P., Lu, J., Thieffry, D., Beato, M., and Graf, T. (2014). C/EBPalpha poises B cells for rapid reprogramming into induced pluripotent stem cells. Nature 506, 235-239.

Doege, C. A., Inoue, K., Yamashita, T., Rhee, D. B., Travis, S., Fujita, R., Guarnieri, P., Bhagat, G., Vanti, W. B., Shih, A., et al. (2012). Early-stage epigenetic modification during somatic cell reprogramming by Parp1 and Tet2. Nature 488, 652-655.

Eminli, S., Foudi, A., Stadtfeld, M., Maherali, N., Ahfeldt, T., Mostoslaysky, G., Hock, H., and Hochedlinger, K. (2009). Differentiation stage determines potential of hematopoietic cells for reprogramming into induced pluripotent stem cells. Nature genetics 41, 968-976.

Esteban, M. A., Wang, T., Qin, B., Yang, J., Qin, D., Cai, J., Li, W., Weng, Z., Chen, J., Ni, S., et al. (2010). Vitamin C enhances the generation of mouse and human induced pluripotent stem cells. Cell stem cell 6, 71-79.

Gailhouste, L. (2012). Isolation and purification method of mouse fetal hepatoblasts. Methods in molecular biology (Clifton, N.J. 826, 33-47.

Guo, S., Zi, X., Schulz, V. P., Cheng, J., Zhong, M., Koochaki, S. H., Megyola, C. M., Pan, X., Heydari, K., Weissman, S. M., et al. (2014). Nonstochastic reprogramming from a privileged somatic cell state. Cell 156, 649-662.

Hu, X., Zhang, L., Mao, S. Q., Li, Z., Chen, J., Zhang, R. R., Wu, H. P., Gao, J., Guo, F., Liu, W., et al. (2014). Tet and TDG mediate DNA demethylation essential for mesenchymal-to-epithelial transition in somatic cell reprogramming. Cell stem cell 14, 512-522.

Kelly, K. F., Ng, D. Y., Jayakumaran, G., Wood, G. A., Koide, H., and Doble, B. W. (2011). beta-catenin enhances Oct-4 activity and reinforces pluripotency through a TCF-independent mechanism. Cell stem cell 8, 214-227.

Koche, R. P., Smith, Z. D., Adli, M., Gu, H., Ku, M., Gnirke, A., Bernstein, B. E., and Meissner, A. (2011). Reprogramming factor expression initiates widespread targeted chromatin remodeling. Cell stem cell 8, 96-105.

Li, W., Jiang, K., Wei, W., Shi, Y., and Ding, S. (2013). Chemical approaches to studying stem cell biology. Cell Res 23, 81-91.

Li, W., Zhou, H., Abujarour, R., Zhu, S., Young Joo, J., Lin, T., Hao, E., Scholer, H. R., Hayek, A., and Ding, S. (2009). Generation of human-induced pluripotent stem cells in the absence of exogenous Sox2. Stem cells (Dayton, Ohio) 27, 2992-3000.

Liang, G., He, J., and Zhang, Y. (2012). Kdm2b promotes induced pluripotent stem cell generation by facilitating gene activation early in reprogramming. Nature cell biology 14, 457-466.

Maherali, N., and Hochedlinger, K. (2009). Tgfbeta signal inhibition cooperates in the induction of iPSCs and replaces Sox2 and cMyc. Curr Biol 19, 1718-1723.

Mansour, A. A., Gafni, O., Weinberger, L., Zviran, A., Ayyash, M., Rais, Y., Krupalnik, V., Zerbib, M., Amann-Zalcenstein, D., Maza, I., et al. (2012). The H3K27 demethylase Utx regulates somatic and germ cell epigenetic reprogramming. Nature 488, 409-413.

Monfort, A., and Wutz, A. (2013). Breathing-in epigenetic change with vitamin C. EMBO reports 14, 337-346.

Nelson, W. J., and Nusse, R. (2004). Convergence of Wnt, beta-catenin, and cadherin pathways. Science (New York, N.Y. 303, 1483-1487.

Onder, T. T., Kara, N., Cherry, A., Sinha, A. U., Zhu, N., Bernt, K. M., Cahan, P., Marcarci, B. O., Unternaehrer, J., Gupta, P. B., et al. (2012). Chromatin-modifying enzymes as modulators of reprogramming. Nature 483, 598-602.

Papp, B., and Plath, K. (2013). Epigenetics of reprogramming to induced pluripotency. Cell 152, 1324-1343.

Polo, J. M., Anderssen, E., Walsh, R. M., Schwarz, B. A., Nefzger, C. M., Lim, S. M., Borkent, M., Apostolou, E., Alaei, S., Cloutier, J., et al. (2012). A molecular roadmap of reprogramming somatic cells into iPS cells. Cell 151, 1617-1632.

Rais, Y., Zviran, A., Geula, S., Gafni, O., Chomsky, E., Viukov, S., Mansour, A. A., Caspi, I., Krupalnik, V., Zerbib, M., et al. (2013). Deterministic direct reprogramming of somatic cells to pluripotency. Nature 502, 65-70.

Rubinfeld, B., Robbins, P., El-Gamil, M., Albert, I., Porfiri, E., and Polakis, P. (1997). Stabilization of beta-catenin by genetic defects in melanoma cell lines. Science (New York, N.Y. 275, 1790-1792.

Silva, J., Barrandon, O., Nichols, J., Kawaguchi, J., Theunissen, T. W., and Smith, A. (2008). Promotion of reprogramming to ground state pluripotency by signal inhibition. PLoS biology 6, e253.

Singhal, N., Graumann, J., Wu, G., Arauzo-Bravo, M. J., Han, D. W., Greber, B., Gentile, L., Mann, M., and Scholer, H. R. (2010). Chromatin-Remodeling Components of the BAF Complex Facilitate Reprogramming. Cell 141, 943-955.

Smith, Z. D., Nachman, I., Regev, A., and Meissner, A. (2010). Dynamic single-cell imaging of direct reprogramming reveals an early specifying event. Nature biotechnology 28, 521-526.

Sommer, C. A., Stadtfeld, M., Murphy, G. J., Hochedlinger, K., Kotton, D. N., and Mostoslaysky, G. (2009). Induced pluripotent stem cell generation using a single lentiviral stem cell cassette. Stem cells (Dayton, Ohio) 27, 543-549.

Soufi, A., Donahue, G., and Zaret, K. S. (2012). Facilitators and impediments of the pluripotency reprogramming factors' initial engagement with the genome. Cell 151, 994-1004.

Stadtfeld, M., and Hochedlinger, K. (2010). Induced pluripotency: history, mechanisms, and applications. Genes & development 24, 2239-2263.

Stadtfeld, M., Maherali, N., Borkent, M., and Hochedlinger, K. (2010). A reprogrammable mouse strain from gene-targeted embryonic stem cells. Nature methods 7, 53-55.

Stadtfeld, M., Maherali, N., Breault, D. T., and Hochedlinger, K. (2008). Defining molecular cornerstones during fibroblast to iPS cell reprogramming in mouse. Cell stem cell 2, 230-240.

Takahashi, K., and Yamanaka, S. (2006). Induction of pluripotent stem cells from mouse embryonic and adult fibroblast cultures by defined factors. Cell 126, 663-676.

Vintersten, K., Monetti, C., Gertsenstein, M., Zhang, P., Laszlo, L., Biechele, S., and Nagy, A. (2004). Mouse in red: red fluorescent protein expression in mouse ES cells, embryos, and adult animals. Genesis 40, 241-246.

Wang, T., Chen, K., Zeng, X., Yang, J., Wu, Y., Shi, X., Qin, B., Zeng, L., Esteban, M. A., Pan, G., et al. (2011). The histone demethylases jhdm1a/1b enhance somatic cell reprogramming in a vitamin-C-dependent manner. Cell stem cell 9, 575-587.

SUPPLEMENTAL REFERENCES

Akashi, K., Traver, D., Miyamoto, T., and Weissman, I. L. (2000). A clonogenic common myeloid progenitor that gives rise to all myeloid lineages. Nature 404, 193-197.

Eggan, K., Akutsu, H., Loring, J., Jackson-Grusby, L., Klemm, M., Rideout, W. M., 3rd, Yanagimachi, R., and Jaenisch, R. (2001). Hybrid vigor, fetal overgrowth, and viability of mice derived by nuclear cloning and tetraploid embryo complementation. Proceedings of the National Academy of Sciences of the United States of America 98, 6209-6214.

Gailhouste, L. (2012). Isolation and purification method of mouse fetal hepatoblasts. Methods in molecular biology (Clifton, N.J. 826, 33-47.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Tu, Y., Stolovitzky, G., and Klein, U. (2002). Quantitative noise analysis for gene expression microarray experiments. Proceedings of the National Academy of Sciences of the United States of America 99, 14031-14036.

What is claimed is:

1. A method for generating induced pluripotent stem cells (iPSCs), the method comprising:
   a) providing at least one somatic cell comprising exogenous nucleic acid sequences encoding reprogramming factors, wherein the reprogramming factors comprise Oct4, Klf4, Sox2 and c-Myc, and
   b) culturing the at least one somatic cell in a first culture medium comprising a combination of agents comprising:
      i) an activator of Wnt signaling comprising CHIR99021,
      ii) an inhibitor of transforming growth factor β (TGF-β), comprising ALK5 inhibitor II, and
      iii) ascorbic acid,
   wherein the combination is in an amount effective to induce somatic cell reprogramming and the at least one somatic cell is cultured for an amount of time sufficient to induce reprogramming of the somatic cells, thereby generating iPSCs.

2. The method of claim 1, wherein the exogenous nucleic acid sequences are introduced via viral transduction or transfection of mRNA or plasmid DNA.

3. The method of claim 1, wherein the exogenous reprogramming factors comprise at least one of Oct4, Klf4, Sox2, and c-Myc.

4. The method of claim 3, wherein the exogenous reprogramming factors comprise Oct4, Klf4, Sox2, and c-Myc.

5. The method of claim 1, wherein the exogenous reprogramming factors comprise at least one of Oct4, Sox2, and Esrrb; at least one of Nr5a1, Sox2, Klf4 and myc; at least one of Sall4, Nanog, Esrrb, Lin28; at least one of Oct4, Sox2 and myc;

and at least one of Tet1, Sox2, Klf4 and myc.

6. The method of claim 1, further comprising transferring the pluripotent cells from the first culture medium to a second culture medium that lacks the activator of Wnt signaling, the inhibitor of transforming growth factor β (TGF-β), and the ascorbic acid.

7. The method of claim 1, wherein the amount of time sufficient to induce reprogramming of the somatic cells is less than six days.

8. The method of claim 1, further comprising selecting the pluripotent cells based on expression of at least one pluripotent marker.

9. The method of claim 8, wherein the at least one pluripotent marker is ESSRB, NANOG, UTF1, endogenous SOX2, or endogenous Oct4 (also called Pou5f1).

10. The method of claim 1, wherein the at least one somatic cell is a fibroblast, keratinocyte, immature or mature blood cell, or mature T or B cell.

11. The method of claim 1, wherein the at least one somatic cell is a mammalian somatic cell.

12. The method of claim 1, wherein the combination of agents in an amount effective to induce somatic cell reprogramming is 0.1 microM to 30 microM of the activator of Wnt signaling, 25 nm to 2000 nm of the inhibitor of TGF-β, and 5 microgram/ml to 200 microgram/ml of ascorbic acid.

13. The method of claim 1, wherein a population of somatic cells is provided and cultured and a reprogramming efficiency of 80% or greater is achieved.

14. The method of claim 1, wherein the amount of time sufficient to induce reprogramming of the somatic cells is less than 7 days.

15. The method of claim 1, wherein the amount of time sufficient to induce reprogramming of the somatic cells is 3-8 days.

16. The method of claim 1 comprising culturing the at least one somatic cell in the first culture medium for an amount of time of less than 7 days to induce reprogramming of the somatic cells, thereby generating iPSCs.

* * * * *

SEQUENCE LISTING

```
<160> NUMBER OF SEQ ID NOS: 16

<210> SEQ ID NO 1
<211> LENGTH: 1084
<212> TYPE: DNA
<213> ORGANISM: Homo sapiens

<400> SEQUENCE: 1
atggcgggac acctggcttc ggatttcgcc ttctcgcccc ctccaggtgg tggaggtgat      60
gggccagggg ggccggagcc gggctgggtt gatcctcgga cctggctaag cttccaaggc     120
cctcctggag ggccaggaat cgggccgggg gttgggccag gctctgaggt gtgggggatt     180
cccccatgcc ccccgccgta tgagttctgt gggggatgg cgtactgtgg gccccaggtt      240
ggagtggggc tagtgcccca aggcggcttg gagacctctc agcctgaggg cgaagcagga     300
gtcggggtgg agagcaactc cgatggggcc tccccggagc cctgcaccgt caccctggt     360 gccgtgaagc tggagaagga gaagctggag caaaacccgg aggagtccca ggacatcaaa     420
gctctgcaga aagaactcga gcaatttgcc aagctcctga agcagaagag gatcaccctg     480
ggatatacac aggccgatgt ggggctcacc ctgggggttc tatttgggaa ggtattcagc     540
caaacgacca tctgccgctt tgaggctctg cagcttagct tcaagaacat gtgtaagctg     600
cggcccttgc tgcagaagtg ggtggaggaa gctgacaaca atgaaaatct tcaggagata     660
tgcaaagcag aaaccctcgt gcaggcccga aagagaaagc gaaccagtat cgagaaccga     720
gtgagaggca acctggagaa tttgttcctg cagtgcccga aacccacact gcagcagatc     780
agccacatcg cccagcagct tgggctcgag aaggatgtgg tccgagtgtg gttctgtaac     840
cggcgccaga agggcaagcg atcaagcagc gactatgcac aacgagagga tttttgaggct     900 gctgggtctc ctttctcagg gggaccagtg tcctttcctc tggccccagg gccccatttt     960 ggtacccag  gctatgggag ccctcacttc actgcactgt actcctcggt cccttttcct    1020 gaggggaag  cctttccccc tgtctctgtc accactctgg gctctcccat gcattcaaac    1080
ttaa                                                                 1084
```

<210> SEQ ID NO 2
<211> LENGTH: 361
<212> TYPE: PRT
<213> ORGANISM: Homo sapiens

<400> SEQUENCE: 2

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn Leu
        355                 360

<210> SEQ ID NO 3

```
<211> LENGTH: 1413
<212> TYPE: DNA
<213> ORGANISM: Homo sapiens

<400> SEQUENCE: 3
atggctgtca gcgacgcgct gctcccatct ttctccacgt tcgcgtctgg cccggcggga      60
agggagaaga cactgcgtca agcaggtgcc ccgaataacc gctggcggga ggagctctcc     120
cacatgaagc gacttccccc agtgcttccc ggccgcccct atgacctggc ggcggcgacc     180
gtggccacag acctggagag cggcggagcc ggtgcggctt gcggcggtag caacctggcg     240
cccctacctc ggagagagac cgaggagttc aacgatctcc tggacctgga ctttattctc     300
tccaattcgc tgacccatcc tccggagtca gtggccgcca ccgtgtcctc gtcagcgtca     360
gcctcctctt cgtcgtcgcc gtcgagcagc ggccctgcca gcgcgccctc cacctgcagc     420
ttcacctatc cgatccgggc cgggaacgac ccgggcgtgg cgccgggcgg cacgggcgga     480
ggcctcctct atggcaggga gtccgctccc cctccgacgg ctcccttcaa cctggcggac     540
atcaacgacg tgagcccctc gggcggcttc gtggccgagc tcctgcggcc agaattggac     600
ccggtgtaca ttccgccgca gcagccgcag ccgccaggtg cgggctgat gggcaagttc      660 gtgctgaagg cgtcgctgag cgcccctggc agcgagtacg cagcccgtc ggtcatcagc      720 gtcagcaaag cagccctga cggcagccac ccggtggtgg tggcgcccta acggcggg       780 ccgccgcgca cgtgccccaa gatcaagcag gaggcggtct cttcgtgcac ccacttgggc     840
gctggacccc ctctcagcaa tggccaccgg ccggctgcac acgacttccc cctggggcgg     900
cagctcccca gcaggactac cccgaccctg ggtcttgagg aagtgctgag cagcagggac     960
tgtcaccctg ccctgccgct tcctcccggc ttccatcccc acccggggcc caattaccca    1020
tccttcctgc ccgatcagat gcagccgcaa gtccgccgc tccattacca agagctcatg     1080
ccacccggtt cctgcatgcc agaggagccc aagccaaaga ggggaagacg atcgtggccc    1140
cggaaaagga ccgccacccca cacttgtgat tacgcgggct gcggcaaaac ctacacaaag    1200
agttcccatc tcaaggcaca cctgcgaacc cacacaggtg agaaaccttta ccactgtgac    1260 tgggacggct gtggatggaa attcgcccgc tcagatgaac tgaccaggca ctaccgtaaa     1320
cacacggggc accgccgtt ccagtgccaa aaatgcgacc gagcattttc caggtcggac     1380
cacctcgcct tacacatgaa gaggcatttt taa                                 1413

<210> SEQ ID NO 4
<211> LENGTH: 470
<212> TYPE: PRT
<213> ORGANISM: Homo sapiens

<400> SEQUENCE: 4
```

Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Ala Thr Val Ala Thr Asp
    50                  55                  60

Leu Glu Ser Gly Gly Ala Gly Ala Ala Cys Gly Gly Ser Asn Leu Ala
65                  70                  75                  80

Pro Leu Pro Arg Arg Glu Thr Glu Glu Phe Asn Asp Leu Leu Asp Leu
                85                  90                  95

Asp Phe Ile Leu Ser Asn Ser Leu Thr His Pro Pro Glu Ser Val Ala
            100                 105                 110

Ala Thr Val Ser Ser Ala Ser Ala Ser Ser Ser Ser Ser Ser Pro Ser
        115                 120                 125

Ser Ser Gly Pro Ala Ser Ala Pro Ser Thr Cys Ser Phe Thr Tyr Pro
130                 135                 140

Ile Arg Ala Gly Asn Asp Pro Val Ala Pro Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Ser Gly Phe Val Ala
            180                 185                 190

Glu Leu Leu Arg Pro Glu Leu Asp Pro Val Tyr Ile Pro Pro Gln Gln
        195                 200                 205

Pro Gln Pro Pro Gly Gly Gly Leu Met Gly Lys Phe Val Leu Lys Ala
    210                 215                 220

Ser Leu Ser Ala Pro Gly Ser Glu Tyr Gly Ser Pro Ser Val Ile Ser
225                 230                 235                 240

Val Ser Lys Gly Ser Pro Asp Gly Ser His Pro Val Val Ala Pro
                245                 250                 255

Tyr Asn Gly Gly Pro Pro Arg Thr Cys Pro Lys Ile Lys Gln Glu Ala
            260                 265                 270

Val Ser Ser Cys Thr His Leu Gly Ala Gly Pro Pro Leu Ser Asn Gly
        275                 280                 285

His Arg Pro Ala Ala His Asp Phe Pro Leu Gly Arg Gln Leu Pro Ser
    290                 295                 300

Arg Thr Thr Pro Thr Leu Gly Leu Glu Glu Val Leu Ser Ser Arg Asp
305                 310                 315                 320

Cys His Pro Ala Leu Pro Leu Pro Pro Gly Phe His Pro His Pro Gly
                325                 330                 335

Pro Asn Tyr Pro Ser Phe Leu Pro Asp Gln Met Gln Pro Gln Val Pro
            340                 345                 350

Pro Leu His Tyr Gln Glu Leu Met Pro Pro Gly Ser Cys Met Pro Glu
        355                 360                 365

Glu Pro Lys Pro Lys Arg Gly Arg Arg Ser Trp Pro Arg Lys Arg Thr
370                 375                 380

Ala Thr His Thr Cys Asp Tyr Ala Gly Cys Gly Lys Thr Tyr Thr Lys
385                 390                 395                 400

Ser Ser His Leu Lys Ala His Leu Arg Thr His Thr Gly Glu Lys Pro
                405                 410                 415

Tyr His Cys Asp Trp Asp Gly Cys Gly Trp Lys Phe Ala Arg Ser Asp
            420                 425                 430

Glu Leu Thr Arg His Tyr Arg Lys His Thr Gly His Arg Pro Phe Gln
        435                 440                 445

Cys Gln Lys Cys Asp Arg Ala Phe Ser Arg Ser Asp His Leu Ala Leu
    450                 455                 460

His Met Lys Arg His Phe
465                 470

<210> SEQ ID NO 5
<211> LENGTH: 955
<212> TYPE: DNA
<213> ORGANISM: Homo sapiens

<400> SEQUENCE: 5

```
atgtacaaca tgatggagac ggagctgaag ccgccgggcc cgcagcaaac ttcggggggc      60
ggcggcggca actccaccgc ggcggcggcc ggcggcaacc agaaaaacag cccggaccgc     120
gtcaagcggc ccatgaatgc cttcatggtg tggtcccgcg ggcagcggcg caagatggcc     180
caggagaacc ccaagatgca caactcggag atcagcaagc gcctgggcgc cgagtggaaa     240
cttttgtcgg agacggagaa gcggccgttc atcgacgagg ctaagcggct gcgagcgctg     300
cacatgaagg agcacccgga ttataaatac cggccccggc ggaaaaccaa gacgctcatg     360
aagaaggata gtacacgct gcccggcggg ctgctggccc ccggcggcaa tagcatggcg     420
agcggggtcg gggtgggcgc cggcctgggc gcgggcgtga accagcgcat ggacagttac     480
gcgcacatga acggctggag caacggcagc tacagcatga tgcaggacca gctgggctac     540
ccgcagcacc cgggcctcaa tgcgcacggc gcagcgcaga tgcagcccat gcaccgctac     600
gacgtgagcg ccctgcagta caactccatg accagctcgc agacctacat gaacggctcg     660
cccacctaca gcatgtccta ctcgcagcag ggcaccctg gcatggctct tggctccatg     720
ggttcggtgg tcaagtccga ggccagctcc agccccctg tggttacctc ttcctcccac     780
tccagggcgc cctgccaggc cggggacctc cgggacatga tcagcatgta ctctccccggc     840
gccgaggtgc cggaacccgc cgcccccagc agacttcaca tgtcccagca ctaccagagc     900
ggcccggtgc ccggcacggc cattaacggc acactgcccc tctcacacat gttaa         955
```

<210> SEQ ID NO 6
<211> LENGTH: 317
<212> TYPE: PRT
<213> ORGANISM: Homo sapiens

<400> SEQUENCE: 6

```
Met Tyr Asn Met Met Glu Thr Glu Leu Lys Pro Pro Gly Pro Gln Gln
 1               5                  10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
```

```
                    195                 200                 205
Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
290                 295                 300

Gly Thr Ala Ile Asn Gly Thr Leu Pro Leu Ser His Met
305                 310                 315

<210> SEQ ID NO 7
<211> LENGTH: 1320
<212> TYPE: DNA
<213> ORGANISM: Homo sapiens

<400> SEQUENCE: 7
atgcccctca acgttagctt caccaacagg aactatgacc tcgactacga ctcggtgcag      60
ccgtatttct actgcgacga ggaggagaac ttctaccagc agcagcagca gagcgagctg     120
cagcccccgg cgcccagcga ggatatctgg aagaaattcg agctgctgcc caccccgccc     180
ctgtccccta gccgccgctc cgggctctgc tcgccctcct acgttgcggt cacacccttc     240
tcccttcggg gagacaacga cggcggtggc gggagcttct ccacggccga ccagctggag     300
atggtgaccg agctgctggg aggagacatg gtgaaccaga gtttcatctg cgacccggac     360
gacgagacct tcatcaaaaa catcatcatc caggactgta tgtggagcgg cttctcggcc     420
gccgccaagc tcgtctcaga aagctggcc tcctaccagg ctgcgcgcaa agacagcggc     480
agcccgaacc ccgccgcgg ccacagcgtc tgctccacct ccagcttgta cctgcaggat     540
ctgagcgccg ccgcctcaga gtgcatcgac ccctcggtgg tcttccccta ccctctcaac     600
gacagcagct cgcccaagtc ctgcgcctcg caagactcca gcgccttctc tccgtcctcg     660
gattctctgc tctcctcgac ggagtcctcc ccgcagggca gccccgagcc cctggtgctc     720
catgaggaga caccgcccac caccagcagc gactctgagg aggaacaaga agatgaggaa     780
gaaatcgatg ttgtttctgt ggaaaagagg caggctcctg gcaaaaggtc agagtctgga     840
tcaccttctg ctggaggcca gcaaaacct cctcacagcc cactggtcct caagaggtgc     900
cacgtctcca cacatcagca aactacgca gcgcctccct ccactcggaa ggactatcct     960
gctgccaaga gggtcaagtt ggacagtgtc agagtcctga cagatcag caacaaccga    1020 aaatgcacca gccccaggtc ctcggacacc gaggagaatg tcaagaggcg aacacacaac    1080
gtcttggagc gccagaggag gaacgagcta aaacggagct ttttgcccct gcgtgaccag    1140
atcccggagt tggaaaacaa tgaaaaggcc cccaaggtag ttatccttaa aaaagccaca    1200
gcatacatcc tgtccgtcca agcagaggag caaaagctca tttctgaaga ggacttgttg    1260
cggaaacgac gagaacagtt gaaacacaaa cttgaacagc tacggaactc ttgtgcgtaa    1320

<210> SEQ ID NO 8
<211> LENGTH: 439
<212> TYPE: PRT
```

<213> ORGANISM: Homo sapiens

<400> SEQUENCE: 8

```
Met Pro Leu Asn Val Ser Phe Thr Asn Arg Asn Tyr Asp Leu Asp Tyr
1               5                   10                  15
Asp Ser Val Gln Pro Tyr Phe Tyr Cys Asp Glu Glu Glu Asn Phe Tyr
            20                  25                  30
Gln Gln Gln Gln Gln Ser Glu Leu Gln Pro Pro Ala Pro Ser Glu Asp
        35                  40                  45
Ile Trp Lys Lys Phe Glu Leu Leu Pro Thr Pro Pro Leu Ser Pro Ser
    50                  55                  60
Arg Arg Ser Gly Leu Cys Ser Pro Ser Tyr Val Ala Val Thr Pro Phe
65                  70                  75                  80
Ser Leu Arg Gly Asp Asn Asp Gly Gly Gly Gly Ser Phe Ser Thr Ala
                85                  90                  95
Asp Gln Leu Glu Met Val Thr Glu Leu Leu Gly Gly Asp Met Val Asn
            100                 105                 110
Gln Ser Phe Ile Cys Asp Pro Asp Asp Glu Thr Phe Ile Lys Asn Ile
        115                 120                 125
Ile Ile Gln Asp Cys Met Trp Ser Gly Phe Ser Ala Ala Ala Lys Leu
    130                 135                 140
Val Ser Glu Lys Leu Ala Ser Tyr Gln Ala Ala Arg Lys Asp Ser Gly
145                 150                 155                 160
Ser Pro Asn Pro Ala Arg Gly His Ser Val Cys Ser Thr Ser Ser Leu
                165                 170                 175
Tyr Leu Gln Asp Leu Ser Ala Ala Ala Ser Glu Cys Ile Asp Pro Ser
            180                 185                 190
Val Val Phe Pro Tyr Pro Leu Asn Asp Ser Ser Ser Pro Lys Ser Cys
        195                 200                 205
Ala Ser Gln Asp Ser Ser Ala Phe Ser Pro Ser Ser Asp Ser Leu Leu
    210                 215                 220
Ser Ser Thr Glu Ser Ser Pro Gln Gly Ser Pro Glu Pro Leu Val Leu
225                 230                 235                 240
His Glu Glu Thr Pro Pro Thr Thr Ser Ser Asp Ser Glu Glu Glu Gln
                245                 250                 255
Glu Asp Glu Glu Glu Ile Asp Val Val Ser Val Glu Lys Arg Gln Ala
            260                 265                 270
Pro Gly Lys Arg Ser Glu Ser Gly Ser Pro Ser Ala Gly Gly His Ser
        275                 280                 285
Lys Pro Pro His Ser Pro Leu Val Leu Lys Arg Cys His Val Ser Thr
    290                 295                 300
His Gln His Asn Tyr Ala Ala Pro Pro Ser Thr Arg Lys Asp Tyr Pro
305                 310                 315                 320
Ala Ala Lys Arg Val Lys Leu Asp Ser Val Arg Val Leu Arg Gln Ile
                325                 330                 335
Ser Asn Asn Arg Lys Cys Thr Ser Pro Arg Ser Ser Asp Thr Glu Glu
            340                 345                 350
Asn Val Lys Arg Arg Thr His Asn Val Leu Glu Arg Gln Arg Arg Asn
        355                 360                 365
Glu Leu Lys Arg Ser Phe Phe Ala Leu Arg Asp Gln Ile Pro Glu Leu
    370                 375                 380
Glu Asn Asn Glu Lys Ala Pro Lys Val Val Ile Leu Lys Lys Ala Thr
385                 390                 395                 400
```

Ala Tyr Ile Leu Ser Val Gln Ala Glu Glu Lys Leu Ile Ser Glu
                405                 410                 415

Glu Asp Leu Leu Arg Lys Arg Glu Gln Leu Lys His Lys Leu Glu
            420                 425                 430

Gln Leu Arg Asn Ser Cys Ala
        435

<210> SEQ ID NO 9
<211> LENGTH: 1059
<212> TYPE: DNA
<213> ORGANISM: Mus musculus

<400> SEQUENCE: 9

```
atggctggac acctggcttc agacttcgcc ttctcacccc caccaggtgg gggtgatggg      60
tcagcagggc tggagccggg ctgggtggat cctcgaacct ggctaagctt ccaagggcct     120
ccaggtgggc ctggaatcgg accaggctca gaggtattgg ggatctcccc atgtccgccc     180
gcatacgagt tctgcggagg gatggcatac tgtggacctc aggttggact gggcctagtc     240
ccccaagttg gcgtggagac tttgcagcct gagggccagg caggagcacg agtggaaagc     300
aactcagagg gaacctcctc tgagccctgt gccgaccgcc caatgccgt gaagttggag      360
aaggtggaac caactcccga ggagtcccag acatgaaag ccctgcagaa ggagctagaa      420
cagtttgcca agctgctgaa gcagaagagg atcaccttgg ggtacaccca ggccgacgtg     480
gggctcaccc tgggcgttct ctttggaaag gtgttcagcc agaccaccat ctgtcgcttc     540
gaggccttgc agctcagcct taagaacatg tgtaagctgc ggcccctgct ggagaagtgg     600
gtggaggaag ccgacaacaa tgagaacctt caggagatat gcaaatcgga gaccctggtg     660
caggcccgga agaaaagcg aactagcatt gagaaccgtg tgaggtggag tctggagacc     720
atgtttctga agtgcccgaa gccctcccta cagcagatca ctcacatcgc caatcagctt     780
gggctagaga aggatgtggt tcgagtatgg ttctgtaacc ggcgccagaa gggcaaaaga     840
tcaagtattg agtattccca acgagaagag tatgaggcta cagggacacc tttcccaggg     900
ggggctgtat cctttcctct gcccccaggt ccccactttg caccccagg ctatggaagc      960
ccccacttca ccacactcta ctcagtccct tttcctgagg cgaggccttt ccctctgtt     1020
cccgtcactg ctctgggctc tcccatgcat tcaaactaa                            1059
```

<210> SEQ ID NO 10
<211> LENGTH: 352
<212> TYPE: PRT
<213> ORGANISM: Mus musculus

<400> SEQUENCE: 10

Met Ala Gly His Leu Ala Ser Asp Phe Ala Phe Ser Pro Pro Gly
1               5                   10                  15

Gly Gly Asp Gly Ser Ala Gly Leu Glu Pro Gly Trp Val Asp Pro
            20                  25                  30

Thr Trp Leu Ser Phe Gln Gly Pro Gly Gly Pro Gly Ile Gly Pro
        35                  40                  45

Gly Ser Glu Val Leu Gly Ile Ser Pro Cys Pro Pro Ala Tyr Glu Phe
    50                  55                  60

Cys Gly Gly Met Ala Tyr Cys Gly Pro Gln Val Gly Leu Gly Leu Val
65                  70                  75                  80

Pro Gln Val Gly Val Glu Thr Leu Gln Pro Glu Gly Gln Ala Gly Ala
                85                  90                  95

```
Arg Val Glu Ser Asn Ser Glu Gly Thr Ser Ser Glu Pro Cys Ala Asp
            100                 105                 110
Arg Pro Asn Ala Val Lys Leu Glu Lys Val Glu Pro Thr Pro Glu Glu
        115                 120                 125
Ser Gln Asp Met Lys Ala Leu Gln Lys Glu Leu Glu Gln Phe Ala Lys
    130                 135                 140
Leu Leu Lys Gln Lys Arg Ile Thr Leu Gly Tyr Thr Gln Ala Asp Val
145                 150                 155                 160
Gly Leu Thr Leu Gly Val Leu Phe Gly Lys Val Phe Ser Gln Thr Thr
                165                 170                 175
Ile Cys Arg Phe Glu Ala Leu Gln Leu Ser Leu Lys Asn Met Cys Lys
            180                 185                 190
Leu Arg Pro Leu Leu Glu Lys Trp Val Glu Glu Ala Asp Asn Asn Glu
        195                 200                 205
Asn Leu Gln Glu Ile Cys Lys Ser Glu Thr Leu Val Gln Ala Arg Lys
    210                 215                 220
Arg Lys Arg Thr Ser Ile Glu Asn Arg Val Arg Trp Ser Leu Glu Thr
225                 230                 235                 240
Met Phe Leu Lys Cys Pro Lys Pro Ser Leu Gln Gln Ile Thr His Ile
                245                 250                 255
Ala Asn Gln Leu Gly Leu Glu Lys Asp Val Val Arg Val Trp Phe Cys
            260                 265                 270
Asn Arg Arg Gln Lys Gly Lys Arg Ser Ser Ile Glu Tyr Ser Gln Arg
        275                 280                 285
Glu Glu Tyr Glu Ala Thr Gly Thr Pro Phe Pro Gly Gly Ala Val Ser
    290                 295                 300
Phe Pro Leu Pro Pro Gly Pro His Phe Gly Thr Pro Gly Tyr Gly Ser
305                 310                 315                 320
Pro His Phe Thr Thr Leu Tyr Ser Val Pro Phe Pro Glu Gly Glu Ala
                325                 330                 335
Phe Pro Ser Val Pro Val Thr Ala Leu Gly Ser Pro Met His Ser Asn
                340                 345                 350

<210> SEQ ID NO 11
<211> LENGTH: 1425
<212> TYPE: DNA
<213> ORGANISM: Mus musculus

<400> SEQUENCE: 11
atggctgtca gcgacgctct gctcccgtcc ttctccacgt tcgcgtccgg cccggcggga      60
agggagaaga cactgcgtcc agcaggtgcc ccgactaacc gttggcgtga ggaactctct     120
cacatgaagc gacttccccc acttcccggc cgcccctacg acctggcggc gacggtggcc     180
acagacctgg agagtggcgg agctggtgca gcttgcagca gtaacaaccc ggccctccta     240
gcccggaggg agaccgagga gttcaacgac ctcctggacc tagactttat cctttccaac     300
tcgctaaccc accaggaatc ggtggccgcc accgtgacca cctcggcgtc agcttcatcc     360
tcgtcttccc cagcgagcag cggccctgcc agcgcgccct ccacctgcag cttcagctat     420
ccgatccggg ccgggggtga cccggggcgtg gctgccagca cacaggtgg agggctcctc     480
tacagccgag aatctgcgcc acctcccacg gcccccttca acctggcgga catcaatgac     540
gtgagcccct cgggcggctt cgtggctgag ctcctgcggc ggagttggac cccagtatac     600
attccgccac agcagcctca gccgccaggt ggcgggctga tgggcaagtt tgtgctgaag     660
gcgtctctga ccaccccctgg cagcgagtac agcagccctt cggtcatcag tgttagcaaa     720
```

```
ggaagcccag acggcagcca ccccgtggta gtggcgccct acagcggtgg cccgccgcgc    780
atgtgcccca agattaagca agaggcggtc ccgtcctgca cggtcagccg gtccctagag    840
gcccatttga gcgctggacc ccagctcagc aacggccacc ggcccaacac acacgacttc    900
cccctggggc ggcagctccc caccaggact acccctacac tgagtcccga ggaactgctg    960
aacagcaggg actgtcaccc tggcctgcct cttcccccag gattccatcc ccatccgggg   1020
cccaactacc ctcctttcct gccagaccag atgcagtcac aagtcccctc tctccattat   1080
caagagctca tgccaccggg ttcctgcctg ccagaggagc ccaagccaaa gaggggaaga   1140
aggtcgtggc cccggaaaag aacagccacc cacacttgtg actatgcagg ctgtggcaaa   1200
acctatacca agagttctca tctcaaggca cacctgcgaa ctcacacagg cgagaaacct   1260
taccactgtg actgggacgg ctgtgggtgg aaattcgccc gctccgatga actgaccagg   1320
cactaccgca aacacacagg gcaccggccc tttcagtgcc agaagtgtga cagggccttt   1380
tccaggtcgg accaccttgc cttacacatg aagaggcact tttaa                    1425
```

<210> SEQ ID NO 12
<211> LENGTH: 474
<212> TYPE: PRT
<213> ORGANISM: Mus musculus

<400> SEQUENCE: 12

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Pro Ala Gly Ala Pro Thr
            20                  25                  30

Asn Arg Trp Arg Glu Glu Leu Ser His Met Lys Arg Leu Pro Pro Leu
        35                  40                  45

Pro Gly Arg Pro Tyr Asp Leu Ala Ala Thr Val Ala Thr Asp Leu Glu
    50                  55                  60

Ser Gly Gly Ala Gly Ala Ala Cys Ser Ser Asn Asn Pro Ala Leu Leu
65                  70                  75                  80

Ala Arg Arg Glu Thr Glu Glu Phe Asn Asp Leu Leu Asp Leu Asp Phe
                85                  90                  95

Ile Leu Ser Asn Ser Leu Thr His Gln Glu Ser Val Ala Ala Thr Val
            100                 105                 110

Thr Thr Ser Ala Ser Ala Ser Ser Ser Ser Pro Ala Ser Ser Gly
        115                 120                 125

Pro Ala Ser Ala Pro Ser Thr Cys Ser Phe Ser Tyr Pro Ile Arg Ala
    130                 135                 140

Gly Gly Asp Pro Gly Val Ala Ala Ser Asn Thr Gly Gly Gly Leu Leu
145                 150                 155                 160

Tyr Ser Arg Glu Ser Ala Pro Pro Thr Ala Pro Phe Asn Leu Ala
                165                 170                 175

Asp Ile Asn Asp Val Ser Pro Ser Gly Gly Phe Val Ala Glu Leu Leu
            180                 185                 190

Arg Pro Glu Leu Asp Pro Val Tyr Ile Pro Pro Gln Gln Pro Gln Pro
        195                 200                 205

Pro Gly Gly Gly Leu Met Gly Lys Phe Val Leu Lys Ala Ser Leu Thr
    210                 215                 220

Thr Pro Gly Ser Glu Tyr Ser Ser Pro Ser Val Ile Ser Val Ser Lys
225                 230                 235                 240

Gly Ser Pro Asp Gly Ser His Pro Val Val Val Ala Pro Tyr Ser Gly
```

```
            245                 250                 255
Gly Pro Pro Arg Met Cys Pro Lys Ile Lys Gln Glu Ala Val Pro Ser
            260                 265                 270

Cys Thr Val Ser Arg Ser Leu Glu Ala His Leu Ser Ala Gly Pro Gln
            275                 280                 285

Leu Ser Asn Gly His Arg Pro Asn Thr His Asp Phe Pro Leu Gly Arg
            290                 295                 300

Gln Leu Pro Thr Arg Thr Thr Pro Thr Leu Ser Pro Glu Glu Leu Leu
305                 310                 315                 320

Asn Ser Arg Asp Cys His Pro Gly Leu Pro Leu Pro Pro Gly Phe His
                    325                 330                 335

Pro His Pro Gly Pro Asn Tyr Pro Pro Phe Leu Pro Asp Gln Met Gln
            340                 345                 350

Ser Gln Val Pro Ser Leu His Tyr Gln Glu Leu Met Pro Pro Gly Ser
            355                 360                 365

Cys Leu Pro Glu Glu Pro Lys Pro Lys Arg Gly Arg Arg Ser Trp Pro
            370                 375                 380

Arg Lys Arg Thr Ala Thr His Thr Cys Asp Tyr Ala Gly Cys Gly Lys
385                 390                 395                 400

Thr Tyr Thr Lys Ser Ser His Leu Lys Ala His Leu Arg Thr His Thr
                    405                 410                 415

Gly Glu Lys Pro Tyr His Cys Asp Trp Asp Gly Cys Gly Trp Lys Phe
            420                 425                 430

Ala Arg Ser Asp Glu Leu Thr Arg His Tyr Arg Lys His Thr Gly His
            435                 440                 445

Arg Pro Phe Gln Cys Gln Lys Cys Asp Arg Ala Phe Ser Arg Ser Asp
            450                 455                 460

His Leu Ala Leu His Met Lys Arg His Phe
465                 470

<210> SEQ ID NO 13
<211> LENGTH: 960
<212> TYPE: DNA
<213> ORGANISM: Mus musculus

<400> SEQUENCE: 13
atgtataaca tgatggagac ggagctgaag ccgccgggcc cgcagcaagc ttcgggggc      60 ggcggcggag gaggcaacgc cacggcggcg gcgaccggcg gcaaccagaa gaacagcccg     120
gaccgcgtca gaggcccat gaacgccttc atggtatggt cccggggca gcggcgtaag      180 atggcccagg agaaccccaa gatgcacaac tcggagatca gcaagcgcct gggcgcggag     240
tggaaacttt tgtccgagac cgagaagcgg ccgttcatcg acgaggccaa gcggctgcgc     300
gctctgcaca tgaaggagca cccggattat aaataccggc cgcggcggaa aaccaagacg     360
ctcatgaaga aggataagta cacgcttccc ggaggcttgc tggcccccgg cgggaacagc     420
atggcgagcg gggttggggt gggcgccggc ctgggtgcgg cgtgaaccag cgcatggac      480 agctacgcgc acatgaacgg ctggagcaac ggcagctaca gcatgatgca ggagcagctg     540
ggctacccgc agcaccccggg cctcaacgct acggcgcgg acagatgca accgatgcac      600 cgctacgacg tcagcgccct gcagtacaac tccatgacca gctcgcagac ctacatgaac     660
ggctcgccca cctacagcat gtcctactcg cagcagggca ccccggtat ggcgctgggc      720 tccatgggct ctgtggtcaa gtccgaggcc agctccagcc ccccgtggt tacctcttcc      780 tcccactcca gggcgccctg ccaggccggg gacctccggg acatgatcag catgtacctc     840
```

```
cccggcgccg aggtgccgga gcccgctgcg cccagtagac tgcacatggc ccagcactac    900
cagagcggcc cggtgcccgg cacggccatt aacggcacac tgcccctgtc gcacatgtaa    960
```

<210> SEQ ID NO 14
<211> LENGTH: 319
<212> TYPE: PRT
<213> ORGANISM: Mus musculus

<400> SEQUENCE: 14

Met Tyr Asn Met Met Glu Thr Glu Leu Lys Pro Pro Gly Pro Gln Gln
1               5                   10                  15

Ala Ser Gly Gly Gly Gly Gly Gly Asn Ala Thr Ala Ala Ala Ala Thr
            20                  25                  30

Gly Gly Asn Gln Lys Asn Ser Pro Asp Arg Val Lys Arg Pro Met Asn
        35                  40                  45

Ala Phe Met Val Trp Ser Arg Gly Gln Arg Arg Lys Met Ala Gln Glu
    50                  55                  60

Asn Pro Lys Met His Asn Ser Glu Ile Ser Lys Arg Leu Gly Ala Glu
65                  70                  75                  80

Trp Lys Leu Leu Ser Glu Thr Glu Lys Arg Pro Phe Ile Asp Glu Ala
                85                  90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
        115                 120                 125

Leu Pro Gly Gly Leu Leu Ala Pro Gly Gly Asn Ser Met Ala Ser Gly
    130                 135                 140

Val Gly Val Gly Ala Gly Leu Gly Ala Gly Val Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Asp Val Ser Ala Leu Gln
        195                 200                 205

Tyr Asn Ser Met Thr Ser Ser Gln Thr Tyr Met Asn Gly Ser Pro Thr
    210                 215                 220

Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Ser Pro Pro Val
                245                 250                 255

Val Thr Ser Ser Ser His Ser Arg Ala Pro Cys Gln Ala Gly Asp Leu
            260                 265                 270

Arg Asp Met Ile Ser Met Tyr Leu Pro Gly Ala Glu Val Pro Glu Pro
        275                 280                 285

Ala Ala Pro Ser Arg Leu His Met Ala Gln His Tyr Gln Ser Gly Pro
    290                 295                 300

Val Pro Gly Thr Ala Ile Asn Gly Thr Leu Pro Leu Ser His Met
305                 310                 315

<210> SEQ ID NO 15
<211> LENGTH: 1320
<212> TYPE: DNA
<213> ORGANISM: Mus musculus

<400> SEQUENCE: 15

```
atgcccctca acgtgaactt caccaacagg aactatgacc tcgactacga ctccgtacag    60
ccctatttca tctgcgacga ggaagagaat ttctatcacc agcaacagca gagcgagctg   120
cagccgcccg cgcccagtga ggatatctgg aagaaattcg agctgcttcc cacccccgcc   180
ctgtccccga gccgccgctc cgggctctgc tctccatcct atgttgcggt cgctacgtcc   240
ttctccccaa gggaagacga tgacggcggc ggtggcaact tctccaccgc cgatcagctg   300
gagatgatga ccgagttact tggaggagac atggtgaacc agagcttcat ctgcgatcct   360
gacgacgaga ccttcatcaa gaacatcatc atccaggact gtatgtggag cggtttctca   420
gccgctgcca agctggtctc ggagaagctg gcctcctacc aggctgcgcg caaagacagc   480
accagcctga gccccgcccg cgggcacagc gtctgctcca cctccagcct gtacctgcag   540
gacctcaccg ccgccgcgtc cgagtgcatt gaccccctcag tggtctttcc ctacccgctc   600
aacgacagca gctcgcccaa atcctgtacc tcgtccgatt ccacggcctt ctctccttcc   660
tcggactcgc tgctgtcctc cgagtcctcc ccacgggcca gccctgagcc cctagtgctg   720
catgaggaga caccgcccac caccagcagc gactctgaag aagagcaaga agatgaggaa   780
gaaattgatg tggtgtctgt ggagaagagg caaaccccctg ccaagaggtc ggagtcgggc   840
tcatctccat cccgaggcca cagcaaacct ccgcacagcc cactggtcct caagaggtgc   900
cacgtctcca ctcaccagca aactacgcc gcaccccccct ccacaaggaa ggactatcca   960
gctgccaaga gggccaagtt ggacagtggc agggtcctga agcagatcag caacaaccgc  1020
aagtgctcca gccccaggtc ctcagacacg gaggaaaacg acaagaggcg acacacaac   1080
gtcttggaac gtcagaggag gaacgagctg aagcgcagct tttttgccct gcgtgaccag  1140
atccctgaat tggaaaacaa cgaaaaggcc cccaaggtag tgatcctcaa aaagccacc   1200
gcctacatcc tgtccattca agcagacgag cacaagctca cctctgaaaa ggacttattg  1260
aggaaacgac gagaacagtt gaaacacaaa ctcgaacagc ttcgaaactc tggtgcataa  1320
```

<210> SEQ ID NO 16
<211> LENGTH: 439
<212> TYPE: PRT
<213> ORGANISM: Mus musculus

<400> SEQUENCE: 16

```
Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Asn Phe Tyr
            20                  25                  30

His Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
```

-continued

```
            130                 135                 140
Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
                180                 185                 190

Ser Val Val Phe Pro Tyr Pro Leu Asn Asp Ser Ser Ser Pro Lys Ser
                195                 200                 205

Cys Thr Ser Ser Asp Ser Thr Ala Phe Ser Pro Ser Ser Asp Ser Leu
                210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
                260                 265                 270

Pro Ala Lys Arg Ser Glu Ser Gly Ser Ser Pro Ser Arg Gly His Ser
                275                 280                 285

Lys Pro Pro His Ser Pro Leu Val Leu Lys Arg Cys His Val Ser Thr
                290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335

Ser Asn Asn Arg Lys Cys Ser Ser Pro Arg Ser Ser Asp Thr Glu Glu
                340                 345                 350

Asn Asp Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
                370                 375                 380

Glu Asn Asn Glu Lys Ala Pro Lys Val Val Ile Leu Lys Lys Ala Thr
385                 390                 395                 400

Ala Tyr Ile Leu Ser Ile Gln Ala Asp Glu His Lys Leu Thr Ser Glu
                405                 410                 415

Lys Asp Leu Leu Arg Lys Arg Arg Glu Gln Leu Lys His Lys Leu Glu
                420                 425                 430

Gln Leu Arg Asn Ser Gly Ala
                435
```